(12) United States Patent
Moss et al.

(10) Patent No.: US 7,923,535 B2
(45) Date of Patent: *Apr. 12, 2011

(54) TRYPTOPHAN AS A FUNCTIONAL REPLACEMENT FOR ADP-RIBOSE-ARGININE IN RECOMBINANT PROTEINS

(75) Inventors: Joel Moss, Bethesda, MD (US); Linda Stevens, Gaithersburg, MD (US); Christelle Bourgeois, Bethesda, MD (US); Rita Bortell, Shirley, MA (US)

(73) Assignees: The United States of America as represented by the Secretary of the Department of Health and Human Services, Washington, DC (US); University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/430,023

(22) Filed: Apr. 24, 2009

(65) Prior Publication Data
US 2009/0203878 A1 Aug. 13, 2009

Related U.S. Application Data

(63) Continuation of application No. 10/517,565, filed as application No. PCT/US03/020498 on Jun. 27, 2003, now Pat. No. 7,541,139.

(60) Provisional application No. 60/393,033, filed on Jun. 28, 2002.

(51) Int. Cl.
*A61K 39/00* (2006.01)
*A61K 39/38* (2006.01)
*C07K 14/00* (2006.01)

(52) U.S. Cl. .................. 530/350; 424/184.1; 424/185.1

(58) Field of Classification Search .................. None
See application file for complete search history.

(56) References Cited

U.S. PATENT DOCUMENTS

| | | | | |
|---|---|---|---|---|
| 4,965,190 | A * | 10/1990 | Woo et al. .......................... | 435/6 |
| 5,386,021 | A | 1/1995 | Moss et al. | |
| 5,459,128 | A * | 10/1995 | Rollins et al. ..................... | 514/8 |
| 5,514,600 | A | 5/1996 | Moss et al. | |
| 5,716,816 | A | 2/1998 | Moss et al. | |
| 5,834,310 | A | 11/1998 | Moss et al. | |
| 6,015,668 | A | 1/2000 | Hughes et al. | |
| 7,541,139 | B2 * | 6/2009 | Moss et al. ........................ | 435/4 |
| 2003/0148936 | A1 | 8/2003 | Svendsen et al. | |

FOREIGN PATENT DOCUMENTS

WO WO 01/09174 2/2001

OTHER PUBLICATIONS

Bortell et al., "Levels of Art2+ Cells but not Soluble Art2 Protein Correlate with Expression of Autoimmune Diabetes in the BB Rat," *Autoimmunity*, 33:199-211 (2001).
Bortell et al., "Nicotinamide Adenine Dinucleotide (NAD) and Its Metabolites Inhibit T Lymphocyte Proliferation: Role of Cell Surface NAD Glycohydrolase and Pyrophosphatase Activities[1]," *The Journal of Immunology*, 167(4):2049-2059 (2001).
Moss et al., "Characterization of NAD:arginine ADP-ribosyltransferases," *Molecular and Cellular Biochemistry*, 193:109-113 (1999).
Balducci et al., "Selective Expression of RT6 Superfamily in Human Bronchial Epithelial Cells," *Am. J. Respir. Cell Mol. Biol.* 21:337-346, 1999.
Bals et al., "Epithelial antimicrobial peptides in host defense against infection," *Respiratory Research*, 1(3):141-150, 2000.
Bauer et al., "Structure determination of human and murine β-defensins reveals structural conservation in the absence of significant sequence similarity," *Prot. Sci.*, 10:2470-2479, 2001.
Bortel et al., "Levels of Art2+ cells but not soluble Art2 protein correlate with expression of autoimmune diabetes in the BB rat," *Automimmunity*, 33(3):199-211, 2001, Abstract only.
Bortell et al., "Nicotinamide adenine dinucleotide (NAD) and its metabolites inhibit T lymphocyte proliferation: role of cell surface NAD glycohydrolase and pyrophosphatase activities," *J. Immunol.* 167(4):2049-2059, 2001, Abstract only.
Bourgeois et al., "Identification of Regulatory Domains in ADP-ribosyltransferase-1 That Determine Transferase and NAD Glycohydrolase Activities," 278(29):26351-26355, 2003.
Bredehorst et al., "Using secondary structure predictions and site-directed mutagenesis to identify and probe the role of potential active site motifs in the RT6 mono(ADP-ribosyl)transferase," *Adv Exp Med Biol* 419:185-189, 1997, Abstract only.
Domenighini et al., "Three conserved consensus sequences identify the NAD-binding site of ADP-ribosylating enzymes, expressed by eukaryotes, bacteria and T-even bacteriophages," *Mol. Microbiol.* 21(4):667-674, 1996, Abstract only.
GenBank Accession No. NP_001916, Oct. 26, 2004.
GenBank Accession No. NP_001917, Oct. 26, 2004.
GenBank Accession No. NP_066290, Oct. 26, 2004.
GenBank Accession No. P11479, Sep. 15, 2003.
Greiner et al., Absence of the RT-6 T cell subset in diabetes-prone BB/W rats, *J. Immunol.* 136(1):148-151, 1986, Abstract only.
Haag et al., "Premature stop codons inactivate the RT6 genes of the human and chimpanzee species," *J. Mol. Biol.* 243(3):537-546, 1994, abstract only.
Han et al., "Regulation of NAD+ glycohydrolase activity by NAD+ -dependent auto-ADP-ribosylation," *Biochem. J.* 318:903-908, 1996.
Hara et al., "Glutamic Acid 207 in Rodent T-cell RT6 Antigens Is Essential for Arginine-specific ADP-ribosylation," *J. Biol. Chem.* 271(47):29552-29555, 1996.

(Continued)

*Primary Examiner* — Mark Navarro
(74) *Attorney, Agent, or Firm* — Klarquist Sparkman, LLP.

(57) ABSTRACT

A method is disclosed for producing a polypeptide with a modified activity or stability, by replacing an arginine residue capable of being ADP-ribosylated with a tryptophan or a phenylalanine. In one embodiment, compositions are provided that include polypeptides, such as alpha defensin, with arginine-to-tryptophan or arginine-to-phenylalanine substitutions, where the arginine residue is capable of being ADP-ribosylated. In another embodiment, methods are disclosed for modifying an immune response in a subject.

23 Claims, 6 Drawing Sheets

OTHER PUBLICATIONS

Hara et al., "Mouse Rt6.1 is a thiol-dependent arginine-specific ADP-ribodyltransferase," *Eur. J. Biochem.* 259:289-294, 1999.

Karsten et al., "Expression and comparative analysis of recombinant rat and mouse RT6 T cell mono(ADP-ribosyl)transferase in *E. coli*," *Adv. Exp. Med. Biol.* 419:175-180, 1997, Abstract only.

Koch et al., "The rat T-cell differentiation marker RT6.1 is more polymorphic than its alloantigenic counterpart RT6.2," *Immunology* 65(2):259-265, 1988, Abstract only.

Koch-Nolte et al., "Mouse T Cell Membrane Proteins Rt6-1 and Rt6-2 Are Arginine/Protein Mono(ADPribosyl)transferases and Share Seocndary Structure Motifs with ADP-ribosylating Bacterial Toxins," *J. Biol. Chem.* 271(13):7686-7693, 1996.

Lehrer et al., "Defensins of vertebrate animals," *Curr. Opin. Immunol*, 14:96-102, 2002.

Lesma et al., "Characterization of High Density Lipoprotein-Bound and Soluble RT6 Released Following Administration of Anti-RT6.1 Monoclonal Antibody," *J. Immunol.* 161:1212-1219, 1998.

Maehama et al., "Increase in ADP-ribosyltransferase activity of rat T lymphocyte alloantigen RT6.1 by a single amino acid mutation," *FEBS Lett* 388(2-3):189-191, 1996, Abstract only.

Maehama et al., "Molecular characterization of rat T lymphocyte alloantigen RT6.1 as an ADP-ribosyltransferase," *Adv Exp Med Biol* 419:181-183, 1997, Abstract only.

Maehama et al., "NAD$^+$-dependent ADP-ribosylation of T Lymphocyte Alloantigen RT6.1 Reversibly Proceeding in Intact Rat Lymphocytes," *J. Biol. Chem.* 270(39):22747-22751, 1995.

Mojcik et al., "Characterization of RT6-bearing rat lymphocytes. II. Developmental relationships of RT6- and RT6+ T cells," *Dev Immunol.* 1(3):191-201, 1991, Abstract only.

Moss et al., "ADP-ribosylargine hydrolases and ADP-ribosyltransferases. Partners in ADP-ribosylation cycles," *Adv. Exp. Med. Biol.* 419:25-33, 1997, Abstract only.

Moss et al., "Characterization of Mouse Rt6.1 NAD:Arginine ADP-ribosyltransferase," *J. Biol. Chem.* 272(7):4342-4346, 1997.

Moss et al., "Characterization of NAD: arginine ADP-ribosyltransferases," *Mol Cell Biochem* 193(1-2):109-113, 1999, Abstract only.

Nemoto et al., "Cell surface ADP-ribosyltransferase regulates lymphocyte function-associated molecule-1 (LFA-1) function in T cells," *J. Immunol.* 157(8):3341-3349, 1996, Abstract only.

Okazaki et al., "Glycosylphosphatidylinositol-anchored and Secretory Isoforms of Mono-ADP-ribosyltransferases," *J. Biol. Chem.* 273(37):23617-23620, 1998.

Paone et al., "ADP ribosylation of human neutrophil peptide-1 regulates its biological properties," *PNAS* 99(12):8231-8235, 2002.

Pierrard et al., "Site-Directed Mutagenesis of the Target Arginine for ADP-Ribosylation of Nitrogenase Component II in *Rhodobacter capsulatus*," *Biochem. Biophys. Res. Comm.*, 192(3):1223-1229, 1993.

Raj et al., "Large-scale synthesis and functional elements for the antimicrobial activity of defensins," *Biochem. J.*, 347:633-641, 2000.

Rigby et al., "Rat RT6.2 and mouse Rt6 locus 1 are NAD+: arginine ADP ribosyltransferases with auto-DP ribosylation activity," *J Immunol* 156(11):4259-4265, 1996, Abstract only.

Risso, "Leukocyte antimicrobial peptides: multifunctional effector molecules of innate immunity," *J. Leuk. Bio.*, 68:785-792, 2000.

Stevens et al., "Regulatory Role of Arginine 204 in the Catalytic Activity of Rat Alloantigens ART2a and ART2b," *J. Biol. Chem.* 278(22)19591-19596, 2003.

Supplementary Partial European Search Report dated Mar. 13, 2006, issued in European Patent Application No. EP03762212.

Takada et al., "Expression of NAD Glycohydrolase Activity by Rat Mammary Adenocarcinoma Cells Transformed with Rat T Cell Alloantigen RT6.2," *J. Biol. Chem.* 269(13):9420-9423, 1994.

Tani et al., "Defensins act as potent adjuvants that promote cellular and humoral immune responses in mice to a lymphoma idiotype and carrier antigens," *Int. Immuno.*, 12(5):691-700, 2000.

Thiele et al., "Biochemical characterization of the T-cell alloantigen Rt-6.2," *Immunology* 59(2):195-201, 1986, Abstract only.

Tran et al., "Homodimeric ⊖-Defensins from *Rhesus macaque* Leukocytes," *J. Biol. Chem*, 277:3079-3084, 2002.

Waite et al., "The RT6 rat lymphocyte alloantigen circulates in soluble form," *Cell Immunol.* 152(1):82-95, 1993, Abstract only.

Weng et al., "Modification of the ADP-ribosyltransferase and NAD Glycohydrolase Activities of a Mammalian Transferase (ADP-ribosyltransferase 5) by Auto-ADP-ribosylation," *J. Biol. Chem.* 274(45):31797-31803, 1999.

Wilde et al., "Purification and Characterization of Human Neutrophil Peptide 4, a Novel Member of the Defensin Family," *J. Biol. Chem.*, 264(19):11200-11203, 1989.

Yamada et al., "Automodification of arginine-specific ADP-ribosyltransferase purified from chicken peripheral heterophils and alteration of the transferase activity," *Arch Biochem Biophys* 308(1):31-36, 1994, Abstract only.

Yang et al., "Mammalian defensins in immunity: more than just microbicidal," *Trends in Immunology*, 23(6):291-296, 2002.

Zolkiewska et al., "Integrin α7 as Substrate for a Glycosylphosphatidylinositol-anchored ADP-ribosyltransferase on the Surface of Skeletal Muscle Cells," *J. Biol. Chem.* 268(34):25273-25276, 1993.

Zolkiewska et al., "Molecular characterization of NAD:arginine ADP-ribosyltransferase from rabbit skeletal muscle," *Proc. Natl. Acad. Sci. USA* 89:11352-11356, 1992.

* cited by examiner

Figure 1

```
rat ART2a    MPSNICKFFL TWWLIQQVTG LTGPLMLDTA PNAFDDQYEG CVNKMEEKAP    50
rat ART2b    MPSNICKFFL TWWLIQQVTG LTGPLMLDTA PNAFDDQYEG CVNKMEEKAP    50
                                     ▼
rat ART2a    LLLKEDFNKS EKLKVAWEEA KKRWNNIKPS MSYPKGFNDF HGTALVAYTG   100
rat ART2b    LLLQEDFNMN AKLKVAWEEA KKRWNNIKPS RSYPKGFNDF HGTALVAYTG   100
                  3, 4                              2              I
rat ART2a    SIGVDFNRAV REFKENPGQF HYKAFHYYLT RALQLLSNGD CHSVYRGTKT   150
rat ART2b    SIAVDFNRAV REFKENPGQF HYKAFHYYLT RALQLLSNGD CHSVYRGTKT   150
                                         II                   *
rat ART2a    RFHYTGAGSV RFGQFTSSSL SKTVAQSPEF FSDDGTLFII KTCLGVYIKE   200
rat ART2b    RFHYTGAGSV RFGQFTSSSL SKKVAQSQEF FSDHGTLFII KTCLGVYIKE   200
                   III            *
rat ART2a    FSFYPDQEEV LIPGYEVYQK VRTQGYNEIF LDSPKRKKSN YNCLYSSAGT   250
rat ART2b    FSFRPDQEEV LIPGYEVYQK VRTQGYNEIF LDSPKRKKSN YNCLYSSAGA   250
                 1   *
rat ART2a    RESCVSLFLV VLTSLLVQLL CLAEP                              275
rat ART2b    RESCVSLFLV VLPSLLVQLL CLAEP                              275
```

TRYPTOPHAN AS A FUNCTIONAL REPLACEMENT FOR ADP-RIBOSE-ARGININE IN RECOMBINANT PROTEINS

CROSS REFERENCE TO RELATED APPLICATIONS

This is a continuation of U.S. application Ser. No. 10/517,565, filed Dec. 7, 2004 now U.S. Pat. No. 7,541,139, which is the §371 U.S. National Stage of International Application No. PCT/US2003/020498, filed Jun. 27, 2003, which was published in English under PCT Article 21(2), which in turn claims the benefit of U.S. Provisional Application No. 60/393,033, filed Jun. 28, 2002, all of which are incorporated by reference herein in their entirety.

FIELD

The present disclosure relates generally to the modification of proteins to alter protein activity and stability, specifically, to the substitution of phenylalanine or tryptophan for an arginine residue capable of being adenosine-diphosphate (ADP)-ribosylated in a polypeptide sequence.

BACKGROUND

Mono-ADP-ribosylation of arginine residues in proteins is a reversible modification that involves the following steps: (i) the transfer of an ADP-ribose moiety of nicotinamide adenine dinucleotide (NAD) to an arginine residue of a target protein, or to a free arginine residue, by an arginine-specific ADP-ribosyltransferase (ART) and (ii) the cleavage of the bond between ADP-ribose and arginine by an ADP-ribosylarginine hydrolase.

ARTs were first characterized in bacterial toxins, such as cholera toxin, diphtheria toxin, pertussis toxin, and pseudomonas exotoxin A. ADP-ribosyltransferase activity has since been identified in eukaryotic cells. The widespread expression of ARTs in eukaryotes, as well as in prokaryotes, suggests that the cycle of ADP-ribosylation/de-ADP-ribosylation of amino acid residues is widely involved in regulating protein activity. Moreover, specific ADP-ribose acceptors, such as arginine, may serve as regulatory switches. For example, ADP-ribosylation of a specific arginine residue in the dinitrogenase enzyme of the nitrogen-fixing bacteria *Rhodospirillium rubrum* has been shown to regulate the activity of this enzyme.

In eukaryotes, ART activity is linked to regulatory signals for critical cellular processes such as DNA repair and the maintenance of calcium or phosphorylation levels. In humans, altered cellular ADP-ribosylation levels have been linked to a number of diseases including lupus, diabetes and cancer, whereas bacterial toxins, such as cholera toxin and diphtheria toxin, catalyze the ADP-ribosylation of important metabolic or regulatory proteins in their human hosts.

The ability to identify specific amino acids that can be modified in order to regulate the activity of various proteins is critical in the development of medical treatments and therapies. Thus there is a need to identify additional stable protein modifications that have an effect on protein activity.

SUMMARY

Methods of producing a protein with an altered activity or stability are disclosed herein. The method includes replacing an arginine residue capable of being ADP-ribosylated with either a tryptophan (W) residue or a phenylalanine (F) residue, thereby producing a protein with an increased activity or stability. In one embodiment, the protein has an antimicrobial activity and the stability or activity of the protein is increased. In another embodiment, the protein is a defensin polypeptide. Substitution of an arginine capable of being ADP-ribosylated with either a phenylalanine or a tryptophan results in an increased antimicrobial activity of the defensin molecule or increased stability of the defensin molecule. Specific, non-limiting examples of an antimicrobial activity are T cell chemotaxis, promotion of neutrophil recruitment, or cytokine release.

A method is provided for increasing the activity or stability of a defensin polypeptide comprising an arginine residue capable of being ADP-ribosylated. The method includes substituting the arginine residue with a tryptophan or a phenylalanine, thereby increasing the activity or the stability of the defensin polypeptide.

In another embodiment, a method is disclosed for determining if a protein can be stabilized. The method includes determining if an arginine residue in the protein is capable of being ADP-ribosylated. Detection of ADP-ribosylation of the arginine residue indicates that the stability of the protein, such as a protein with antimicrobial activity, can be increased by substituting the arginine capable of being ADP-ribosylated with either a tryptophan or a phenylalanine.

A composition is disclosed herein that includes a polypeptide where at least one arginine residue capable of being ADP-ribosylated is substituted with a tryptophan or a phenylalanine residue. In one embodiment, the protein has an antimicrobial activity. In another embodiment, the protein is a defensin polypeptide. In yet another embodiment, the amino acid substitution increases the activity or stability of the polypeptide.

A pharmaceutical composition is disclosed herein that includes a therapeutically effective amount of a defensin with at least one arginine residue capable of being ribosylated substituted by a tryptophan or a phenylalanine residue.

In another embodiment, a method is provided for increasing an immune response in a subject. The method includes administering to the subject a therapeutically effective amount of a defensin polypeptide comprising an amino acid substitution, wherein the amino acid substitution is a replacement of an arginine capable of being ADP-ribosylated with a tryptophan or a phenylalanine.

The foregoing and other features and advantages will become more apparent from the following detailed description of several embodiments, which proceeds with reference to the accompanying figures.

BRIEF DESCRIPTION OF THE FIGURES

FIG. 1 is a schematic drawing of the deduced amino acid sequences of rat ART2a (RT6.1) and rat ART2b (RT6.2). Identical amino acids are shaded. Arginine 204 and 81 are specific to ART2b. In ART2a, N58 and 58NKSE61 are in a putative consensus glycosylation site not present in ART2b. Regions I, II, and III, believed to participate in formation of the catalytic site in the bacterial toxin and mammalian ADP-ribosyltransferases, are indicated by solid lines and the putative catalytic amino acids by an asterisk. Dotted underlines indicate signal sequences, which are excised during the export into the endoplasmic reticulum (amino terminus) and attachment of the glycosylphosphotidylinositol (GPI) anchor (carboxy terminus).

SEQUENCE LISTING

Figure 2:
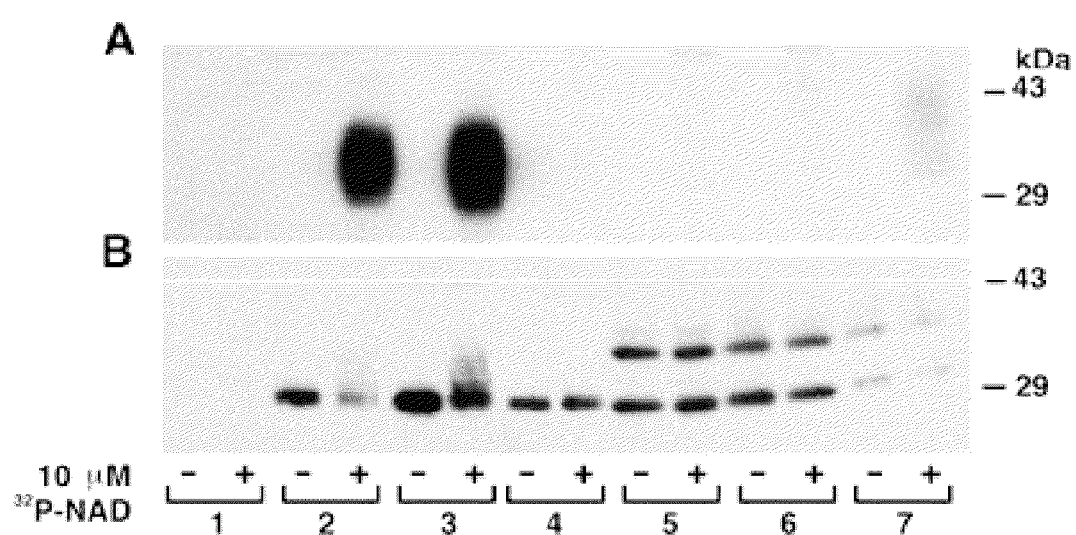
FIG. 2 is a digital image of a set of blots demonstrating the auto-[$^{32}$P]ADP-ribosylation (FIG. 2A) and immunoreactivity (FIG. 2B) of the supernatants from NMU cells transfected with vector alone (lane 1), wild-type ART2b (lane 2), ART2b (R81K) (lane 3), ART2b(R204K) (lane 4), wild-type ART2a (lane 5), ART2a(M81R) (lane 6) and ART2a(Y204R) (lane 7). Data shown are representative of eight independent experiments.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO:1 is the amino acid sequence of the human neutrophil peptide (HNP)-1, HNP-2, HNP-3 prepro-protein.
SEQ ID NO:2 is the amino acid sequence of HNP-1.
SEQ ID NO:3 is the amino acid sequence of HNP-2.
SEQ ID NO:4 is the amino acid sequence of HNP-3.
SEQ ID NO:5 is the amino acid sequence of the HNP-4 prepro-protein.
SEQ ID NO:6 is the amino acid sequence of HNP-4.
SEQ ID NO:7 is the amino acid sequence of the human defensin (HD)-5 prepro-protein.
SEQ ID NO:8 is the amino acid sequence of HD-5.
SEQ ID NO:9 is the amino acid sequence of the HD-6 prepro-protein.
SEQ ID NO:10 is the amino acid sequence of HD-6.
SEQ ID NO:11 is the amino acid sequence of rat ART2a.
SEQ ID NO:12 is the amino acid sequence of rat ART2b.
SEQ ID NO:13 is the primer for introduction of Kozak sequence.
SEQ ID NO:14 is the primer for the ART2a N58A mutation.
SEQ ID NO:15 is the primer for the ART2a K59M, S60N, E61A mutation.
SEQ ID NO:16 is the primer for the ART2a M81R mutation.
SEQ ID NO:17 is the primer for the ART2a Y204R mutation.
SEQ ID NO:18 is the primer for the ART2b R81K mutation.
SEQ ID NO:19 is the primer for the ART2b R204K mutation.
SEQ ID NO:20 is the primer for the ART2b R204E mutation.
SEQ ID NO:21 is the primer for the ART2b R204Y mutation.
SEQ ID NO:22 is the primer for the ART2b R204W mutation.

DETAILED DESCRIPTION

I. Abbreviations
ADP adenosine-diphosphate
ART ADP-ribosyltransferase
ELISA enzyme-linked immunosorbent assay
F phenylalanine
GPI glycosylphosphatidylinositol
HD human defensin
HNP human neutrophil peptide
IL interleukin
M81R methionine-to-arginine substitution at position 81
MIP macrophage inflammatory protein
N58A asparagine-to-alanine substitution at position 58
NAD nicotinamide adenine dinucleotide
NADase nicotinamide adenine dinucleotide glycohydrolase
PI-PLC phosphatidlyinositol specific phospholipase C
R arginine
R81K arginine-to-lysine substitution at position 81
R204E arginine-to-glutamic acid substitution at position 204
R204K arginine-to-lysine substitution at position 204
R204Y arginine-to-tyrosine substitution at position 204
R204W arginine-to-tryptophan substitution at position 204
R:W arginine-to-tryptophan substitution
R:F arginine-to-phenylalanine substitution
W tryptophan
Y204R tyrosine-to-arginine substitution at position 204
59NMA61 asparagine, methionine and alanine at positions 59, 60 and 61, respectively
Standard one-letter codes for amino acids are utilized herein.

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Activity: The biological function of a molecule, such as a polypeptide or a nucleic acid. In one embodiment, an activity is an enzymatic activity. In another embodiment, a biological function is an immunologic activity, such as recruitment of a cell, or cytokine secretion. An activity can be increased or decreased. An increased activity can be, for example, at least about a 20%, about a 50%, about an 80%, about a 100% or about a 200% increase in activity. An activity can also be decreased, such as at least about a 20%, about a 50%, about an 80% or about a 100% decrease in activity. The activity can be increased or decreased as compared to a control, such as the activity of a wildtype protein or a standard value. An activity profile is the set of different activities possessed by a molecule, such as an agent or a drug. A polypeptide can have a single defined activity, or can have several defined activities.

The biological activity of a defensin molecule include modulating T cell chemotaxis and neutrophil recruitment. In one embodiment, an increased antimicrobial activity of a defensin molecule includes increased T cell chemotaxis or increased neutrophil recruitment, as compared to a control defensin molecule under similar conditions.

A specific, non-limiting example of the activity of an ART includes, but is not limited to, NADase activity. In one embodiment, an increased activity of an ART includes increased NADase activity, as compared to a control ART under similar conditions.

ADP-ribosylation: A reaction in which ADP-ribose is covalently attached to a compound. Eukaryotic and prokaryotic mono-ARTs catalyze the transfer of ADP-ribose from nicotinamide adenine dinucleotide (NAD) to an acceptor nucleophile, such as an amino acid (i.e. the guanidino group of an arginine residue). Among the ARTs are bacterial toxins (e.g. cholera toxin, pertussis toxin, diphtheria toxin). Pertussis toxin and diphtheria toxin use amino acids other than arginine as ADP-ribose acceptors.

As disclosed herein, a number of proteins used in host defense are basic and arginine-rich and thus could serve as acceptors for ADP-ribose. These include, but may not be limited to, alpha defensins (HNP-1, HNP-2, HNP-3, HNP-4, HD-5, HD-6); Beta defensins (hBD1, hBD-2, hBD-3, hBD-4); Major Basic Protein; Eosinophil Cationic Protein; and Human Cathelicin LL-37 (hCAP18). In addition, ADP-ribosyltransferases are capable of auto-ADP-ribosylation. These include, but may not be limited to, ART-1, ART2b, ART-3, ART-4, and ART-5.

ADP-ribosyltransferase (ART): An enzyme that catalyzes the transfer of an ADP-ribose from NAD to an acceptor nucleophile. ARTs can be differentiated by their corresponding amino acid targets, which include arginine, cysteine, asparagine, and diphthamide (a post-translationally modified histidine residue). In one embodiment, the ART catalyzes the transfer of ADP-ribose to the guanidino group of an arginine residue on a protein.

Both prokaryotic and eukaryotic ARTs have been identified. Among the prokaryotic ARTs are bacterial toxins (e.g., cholera toxin, pertussis toxin, diphtheria toxin). Five mammalian ARTs (ART-1, ART-2, ART-3, ART-4, ART-5) are known to exist. Substrates of the five known mammalian ARTs include proteins that are involved in critical cellular events (e.g., lymphocyte activation and neutrophil chemotaxis).

A family of mammalian ARTs that are localized on the cell surface through glycosylphosphatidylinositol (GPI) anchors, are expressed preferentially on epithelial and inflammatory cells (for example lymphocytes and neutrophils). ART2a and ART2b are isoenzymes expressed on the surface of mature T cells and intraepithelial lymphocyte cells of the rat. These proteins express both auto-ART and NADase activities, although only ART2b is capable of auto-ADP-ribosylation at multiple sites. Of the two proteins, only ART2a is glycosylated. In addition, both are involved in the transmission of transmembrane signals that modulate T cell activation. Soluble forms of ART have also been identified and circulate in the high-density lipoprotein fraction of serum.

Analysis of the crystallographic structure of bacterial toxin ARTs identified three regions involved in formation of the catalytic site, NAD binding, and activation of the ribosyl-nicotinamide bond, which is required for ADP-ribose transfer. These regions appear to be present in the mammalian transferases as well. Region I is defined by an arginine (R) or histidine (H), Region II, by a sequence rich in hydrophobic amino acids, or by serine (S) X S, (where X represents threonine (T), serine (S) or alanine (A)), and Region III by glutamate (E). (Domenighini et al., *Mol Microbial* 21(4):667-74, 1996; Bredehorst et al., *Adv Exp Med Biol* 419:185-9, 1997; Moss et al., *Mol Cell Biochem* 193(1-2):109-13, 1999; Takada et al., *J Biol Chem* (269(13):9420-3, 1994).

Agent: Any substance, including, but not limited to, a chemical compound, a drug, a small molecule, a peptide mimetic, a peptide or a protein.

Animal: Living multi-cellular vertebrate organisms, a category that includes, for example, mammals and birds. The term mammal includes both human and non-human mammals. Similarly, the term "subject" includes both human and veterinary subjects.

Antimicrobial: A compound, such as an agent or a drug, for killing microorganisms or suppressing their multiplication or growth. An agent has antimicrobial activity if it results in the death of a microorganism or suppresses the growth of a microorganism. In one embodiment, a polypeptide, such as a defensin (i.e. an alpha defensin), has antimicrobial activity. An antimicrobial activity includes, but may not be limited to, cell lysis (e.g. due to cytotoxicity). Antimicrobial activity can result from T cell chemotaxis, and neutrophil recruitment. In one specific example, an antimicrobial activity is the lysis of a bacterial cell. Antimicrobial activity can be modified by the administration of a modified defensin polypeptide. In one embodiment, an R:W substituted, R:F substituted HNP-1 polypeptide, or otherwise modified defensin, is administered to a subject.

Arginine (R): An amino acid ($C_6H_{14}N_4O_2$) found in plants and animals that is essential for the human diet; also produced by the breakdown of proteins. Also encompassed are functional analogues of arginine, and structurally modified arginine molecules (e.g., ADP-ribosylated arginine residues, agmatine) on a guanidine-containing compound, arginine being one such example. An arginine residue that is capable of being ADP-ribosylated is an arginine that can be modified by the transfer of an ADP-ribose from NAD to the guanidino group of an arginine.

Asthma: A disorder of the respiratory system characterized by inflammation, narrowing of the airways and increased reactivity of the airways to inhaled agents. Asthma is frequently, although not exclusively, associated with atopic or allergic symptoms.

B cell or B lymphocyte: One of the two major types of lymphocytes. The antigen receptor on B lymphocytes, sometimes called the B cell receptor, is a cell-surface immunoglobulin. On activation by an antigen, B cells differentiate into cells producing antibody molecules of the same antigen-specificity as this receptor.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Chronic Bronchitis: An inflammation of the lining of the bronchi. When the bronchi are inflamed and/or infected, less air is able to flow to and from the lungs and a heavy mucus or phlegm is coughed up, resulting in bronchitis. A brief attack of acute bronchitis with cough and mucus production can occur with severe colds. Chronic bronchitis is defined by the presence of a mucus-producing cough most days of the month, three months of a year for two successive years without other underlying disease to explain the cough. It may precede or accompany pulmonary emphysema. Cigarette smoking is the most common cause of chronic bronchitis. The bronchi of people with chronic bronchitis may also have been irritated initially by bacterial or viral infections. Air pollution and industrial dusts and fumes are also potential etiologic agents. Once the bronchi have been irritated over a substantial period of time, excessive mucus is produced constantly, the lining of the bronchi becomes thickened, an irritating cough develops, airflow may be hampered, and the lungs are damaged. The bronchi become susceptible to infections.

Crohn's Disease: Crohn's disease is an Inflammatory Bowel Disease (the general name for diseases that cause inflammation in the intestines). Crohn's Disease causes inflammation in the small intestine. Crohn's Disease usually occurs in the lower part of the small intestine (the ileum), but it can affect any part of the digestive tract, from the mouth to the anus. The inflammation extends deep into the lining of the affected organ, causing pain and diarrhea. Crohn's Disease may also be called ileitis or enteritis.

Chronic Obstructive Pulmonary Disease (COPD): Includes emphysema and chronic bronchitis-diseases that are characterized by obstruction to airflow. Emphysema and chronic bronchitis frequently coexist. It does not include other obstructive diseases such as asthma.

Cytokines: Proteins made by cells that affect the behavior of other cells, such as lymphocytes and neutrophils. In one embodiment, a cytokine is a chemokine, a molecule that affects cellular trafficking. Cytokines include, but are not limited to, MIP-$\beta$, interleukin (IL)-1, IL-8, IL-10, granulocyte-macrophage colony stimulating factor (GMCSF), granulocyte colony stimulating factor (GCSF), neurokinin, and tumor necrosis factor-alpha (TNF-$\alpha$).

Defensins: The members of the defensin family are small, cationic peptides that have six conserved cysteine residues that form three disulfide bonds. Functional defensins arise by the sequential post-translational processing of a prepro-protein of 93-95 amino acids. The members of the defensin family are divided into different classes. The alpha-defensins are generally polypeptides containing 29-33 residues. The beta-defensins are more basic than alpha defensins and are generally between 34-37 amino acids in length (Raj et al., *Biochem J.* 347:633-41, 2000). The recently identified theta defensins are formed by the head-to-tail linkage of two alpha defensin-related nonapeptides, generating a circular 18-residue polypeptide (Tang et al., *Science* 286:498-502, 1999).

Defensins were first identified in neutrophils and have been detected in human, rabbit, guinea pig, and rat phagocytes. Alpha defensins include, but are not limited to, HNP-1, HNP-2, HNP-3, HNP-4, human defensin (HD)-5, and HD-6. Alpha defensins also include the recently identified HNP-4 homolog, defensin (Def)-X (see U.S. Pat. No. 6,329,340 herein incorporated by reference). HNP-1, HNP-2, and HNP-3 are products of the same gene (GenBank Accession No. P11479 herein incorporated by reference). HNP-4 is the product of a different gene (GenBank Accession No. NP_001916 herein incorporated by reference). HD-5 (GenBank Accession No. NP_066290) and HD-6, (GenBank Accession No. NP_001917 herein incorporated by reference) are two human enteric defensins.

Defensins are antimicrobial peptides that are toxic for a variety of infectious agents, such as Gram-negative bacteria, Gram-positive bacteria, fungi, and certain enveloped viruses. Defensins act by forming pores in membranes of the infectious agent and generating voltage-dependent channels. Antimicrobial activities of defensins include, but are not limited to, lysis of bacteria, fungi, or viruses; toxicity for bacteria, fungi or viruses; leukocyte (e.g., T cell) chemotaxis; and leukocyte (e.g., neutrophil) recruitment. Without being bound by theory, defensins play an important role in the body's natural immunity against infections. Unmodified defensins are also cytotoxic for several normal and malignant cells.

DNA: Deoxyribonucleic acid. DNA is a long chain polymer which constitutes the genetic material of most living organisms (some viruses have genes composed of ribonucleic acid (RNA)). The repeating units in DNA polymers are four different nucleotides, each of which contains one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequence of three nucleotides in the mRNA that is transcribed from the DNA.

Electrophoretic mobility: The relative distance that a molecule travels in the presence of an electric current.

Emphysema: A condition in which there is over-inflation of structures in the lungs known as alveoli or air sacs. This over-inflation results from a breakdown of the walls of the alveoli, which causes a decrease in respiratory function and often, shortness of breath.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Functionally Equivalent: Sequence alterations, for example in an ADP-ribosyltransferase2 (ART2) polypeptide that do not alter a function of the ART2 polypeptide. In one embodiment, the function is the modulation of T cell activation. In another embodiment, the function is to modulate autoimmunity. Such sequence alterations can include, but are not limited to, substitutions, deletions, base modifications, mutations, labeling, and insertions.

Immune cell: Any cell involved in a host defense mechanism. These can include, for example, T cells, B cells, natural killer cells, neutrophils, mast cells, macrophages, antigen-presenting cells, basophils, eosinophils, and neutrophils.

Immune response: A response of a cell of the immune system, such as a neutrophil, a B cell, or a T cell, to a stimulus. In one embodiment, the immune response involves neutrophil recruitment, the phagocytosis of a microbe by the neutrophil, followed by the release of the contents of the neutrophil's azurophilic granules. In another embodiment, the response is specific for a particular antigen (an "antigen-specific response"). In yet another embodiment, an immune response is an inflammatory response. An immune response can be supplemented by the administration of a modified defensin polypeptide. In one embodiment, an R:W substituted, R:F substituted HNP-1 polypeptide, or otherwise modified defensin, is administered to a subject.

Immune system deficiency: A disease or disorder in which the subject's immune system is not functioning normally, quantitatively or qualitatively, or in which it would be useful to boost a subject's immune response. In another non-limiting example, the subject an immunodeficiency disease resulting from a human immunodeficiency virus (HIV) infection.

Infectious agent: An agent that can infect a subject and/or cause an infection, including, but not limited to, viruses, bacteria, and fungi.

Examples of infectious virus include: Retroviridae (for example, human immunodeficiency viruses, such as HIV-1 (also referred to as HTLV-III, LAV or HTLV-III/LAV, or HIV-III); Paramyxoviridae (for example, parainfluenza viruses, mumps virus, measles virus, respiratory syncytial virus); Orthomyxoviridae (for example, influenza viruses); and Herpesviridae (herpes simplex virus (HSV) 1 and HSV-2, varicella zoster virus, cytomegalovirus (CMV), herpes viruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelli*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Inflammation: When damage to tissue occurs, the body's response to the damage is usually inflammation. The damage can be due to trauma, lack of blood supply, hemorrhage, autoimmunity, transplanted exogenous tissue, or infection. This generalized response by the body includes the release of many components of the immune system (e.g. defensins, IL-1 and tumor necrosis factor), attraction of cells (such as neutrophils) to the site of the damage, swelling of tissue due to the release of fluid, and other processes.

During the inflammatory processes, a variety of soluble factors are involved in leukocyte recruitment through increased expression of cellular adhesion molecules and chemoattraction. Many of these soluble mediators regulate the activation of both the resident cells (such as fibroblasts, endothelial cells, tissue macrophages, and mast cells) and newly recruited inflammatory cells (such as monocytes, lymphocytes, neutrophils, and eosinophils). In one embodiment, activated neutrophils release azurophilic granules that contain defensins. High defensin levels can be found in airway secretions of patients with inflammatory lung diseases.

Inflammatory Bowel Disease: Two separate diseases (Crohn's Disease and Ulcerative Colitis) that cause inflammation of the bowel and can cause arthritis or inflammation in joints. Crohn's Disease involves inflammation of the colon or small intestines. Ulcerative Colitis is characterized by ulcers and inflammation of the lining of the colon. The amount of the bowel disease usually influences the severity of arthritis symptoms.

Innate Immunity: Provides the first line of defense against many common microorganisms and is essential for the control of common bacterial infections. Includes antimicrobial peptides (e.g., defensins), epithelial barriers, phagocytic cells (neutrophils, macrophages), natural killer (NK) cells, the complement system, and cytokines that regulate and coordinate many of the activities of these cells. Defensin polypeptides are present at the surface of epithelial cells, such as those lining the gut and the lungs, and in microbicidal organelles of the phagocytic cells of the hematopoietic system (e.g., neutrophils and macrophages) and therefore are an important component to the innate immune system. Innate immunity can be supplemented by the administration of a modified defensin polypeptide. Thus, an R:W substituted, R:F substituted HNP-1 polypeptide, or otherwise modified defensin, is administered to a subject to increase innate immunity.

Isolated: A biological component (such as a nucleic acid, peptide or protein) that has been substantially separated, produced apart from, or purified away from other biological components in the cell of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases or they may be recruited to the site of infection.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Modified Arginine Residue: Any chemical modification of an arginine. In one embodiment, the modification takes place on the guanidino group of the arginine residue. Modification of the guanidino group includes, but is not limited to, the modification of an arginine residue by ADP-ribosylation, acylation, alkylation, or polymer conjugation. An arginine residue that is ADP ribosylated can be further modified for example, by the pyrophosphatase/phosphatase cleavage of a pyrophosphate to yield a ribosyl-arginine residue. In one embodiment, a decarboxylated arginine residue is a modified arginine residue known as agmatine ($C_5H_{14}N_4$).

Neutrophil: Neutrophils are leukocytes of the Polymorphonuclear Leukocyte subgroup that are also known as granulocytes. Neutrophils contain a lobed nucleus and abundant cytoplasmic granules that stain with neutral dyes. Neutrophils form a primary defense against bacterial infection. Like all the cells of the immune system, neutrophils are produced in the bone marrow and circulate in the bloodstream. However, neutrophils move out of blood vessels into infected tissue in order to engulf and kill microorganisms (e.g., bacteria, fungus, virus). Neutrophils perform their function partially through the phagocytosis of other cells and foreign substances. Neutrophils are recruited to a site of infection by following a concentration gradient of chemoattractants or cytokines.

Nicotinamide adenine dinucleotide glycohydrolase (NADase): An enzyme that catalyzes the hydrolysis of $NAD^+$ to nicotinimide and ADP-ribose. It is present ubiquitously in organisms from bacteria to mammals. NADases found in most eukaryotes are membrane bound and their release by phosphatidyl-inositol-specific phopholipase C suggests that they are anchored to the membrane via a GPI linkage.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

A "therapeutically effective amount" is a quantity of a specific substance sufficient to achieve a desired effect in a subject being treated. For instance, this can be the amount necessary to alter an immune response and/or to inhibit viral, fungal, or bacterial replication or to measurably alter symptoms of the viral, fungal, or bacterial infection. When administered to a subject, a dosage will generally be used that will achieve target tissue concentrations (for example, in lymphocytes) that has been shown to achieve a desired in vitro effect.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15*th* Edition, 1975, describes compositions and formulations suitable for pharmaceutical delivery of modified alpha defensins.

In general, the nature of the carrier will depend on the particular mode of administration employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phenylalanine (F): An amino acid ($C_9H_{12}NO_2$) found in proteins.

Polynucleotide: A linear nucleotide sequence, including sequences of greater than 100 nucleotide bases in length.

Polypeptide: A polymer in which the monomers are amino acid residues that are joined together through amide bonds. Either the L-optical isomer or the D-optical isomer can be used, the L-isomers being preferred in nature. The term polypeptide or protein as used herein encompasses any amino acid sequence and includes, but may not be limited to, modified sequences including, but not limited to, substituted polypeptides, ADP-ribosylated polypeptides, ribosyl-polypeptides, and glycosylated polypeptides. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is for example, at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Preventing or treating a disease: Preventing a disease refers to inhibiting completely or in part the development or progression of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. Treating a disease refers to a therapeutic intervention that ameliorates at least one sign or symptom of a disease or pathological condition, or interferes with a pathophysiological process, after the disease or pathological condition has begun to develop.

Protein: A biological molecule encoded by a gene and comprised of amino acids.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Pyrophosphatase: An enzyme that catalyzes the hydrolysis of pyrophosphate into two phosphate groups.

Recombinant: A recombinant nucleic acid is one that has a sequence that is not naturally occurring or was made artificially. Artificial combination is often accomplished by chemical synthesis or, more commonly, by the artificial manipulation of isolated segments of nucleic acids, e.g., by genetic engineering techniques. Similarly, a recombinant protein is one encoded by a recombinant nucleic acid molecule.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a polypeptide, such as a defensin, and the corresponding cDNA sequence, will possess a relatively high degree of sequence identity when aligned using standard methods. This homology will be more significant when the orthologous proteins or cDNAs are derived from species that are more closely related, compared to species more distantly related (e.g., human and murine sequences).

Methods of alignment of sequences for comparison are well known in the art. Various programs and alignment algorithms are described in Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244 9, 1988); Higgins and Sharp, *CABIOS* 5:151-153, 1989; Corpet et al., *Nuc. Acids Res.* 16:10881-90, 1988; Huang et al., *Computer Appls. in the Biosciences* 8:155-65, 1992; and Pearson et al., *Meth. Mol. Bio.* 24:307-31, 1994. Altschul et al., *J. Mol. Biol.* 215:403-410, 1990, presents a detailed consideration of sequence alignment methods and homology calculations.

Stability: The ability of a substance, such as a polypeptide, to maintain its form, structure or activity. Stability can be increased or decreased. An increased stability is an increase in the ability of a substance, such as a polypeptide, to maintain its form, structure or activity, as compared to a control substance under similar conditions. In one embodiment, the stability of a polypeptide is increased by an amino acid substitution, such as an R:F or an R:W substitution, such as at least about a 20%, 50%, 80%, 100% or 200% increase, as compared to an unsubstituted polypeptide or to a wildtype polypeptide. Stability can be measured by any means known to one of skill in the part, and includes, but is not limited to, measurements of half-life.

Subject: Living multi-cellular vertebrate organisms, a category that includes both human and non-human mammals.

Substitution: The replacement of one amino acid residue with another amino acid residue using any technique known to one of ordinary skill in the art, including site-directed mutagenesis of nucleic acid sequences encoding the amino acid substituted polypeptide or chemical synthesis of the amino acid substituted polypeptide.

Conservative amino acid substitution tables providing functionally similar amino acids are well known to one of ordinary skill in the art. The following six groups are non-limiting examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain.

Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

T cell chemotaxis: The directed locomotion of a T cell along a concentration gradient of chemotactically active factors, such as cytokines. Cells showing positive chemotaxis move towards areas with higher concentrations of these agents, those showing negative chemotaxis move away from these areas.

An increase in T cell chemotaxis includes, but may not be limited to, an increase in the distance or rate of T cell migration, an increase in the number of T cells migrating, an increase in the types of T cells migrating in a sample in response to a chemotactic stimulus, as compared to a control sample which does not receive the chemotactic stimulus.

Therapeutically effective dose: A dose sufficient to prevent advancement, or to cause regression of the disease, or which is capable of relieving symptoms caused by the disease, such as pain or swelling.

Treatment: Refers to both prophylactic inhibition of initial infection or disease, and therapeutic interventions to alter the natural course of an untreated infection or disease process, such as a tumor growth or an infection with a bacteria.

Tryptophan (W): An amino acid ($C_{11}H_{12}N_2O_2$) that is essential for growth and normal metabolism. Tryptophan is a precursor of niacin.

Ulcerative colitis: An Inflammatory Bowel Disease characterized by ulcers and inflammation of the lining of the colon.

Wildtype: The form of a polypeptide or nucleic acid normally found in nature. Also referred to as the native form. In one example, a wildtype polypeptide is a polypeptide where an arginine residue that is capable of being ADP-ribosylated at a position within the amino acid sequence of the polypeptide has not been substituted.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Compositions and Administration of Pharmaceutical Compositions

A composition is provided herein that includes a polypeptide with an arginine-to-tryptophan (R:W) or an arginine-to-phenylalanine (R:F) substitution at a position within the amino acid sequence of the polypeptide, wherein the arginine is capable of being ADP-ribosylated in the unsubstituted form of the polypeptide. Substitution of an arginine residue with a tryptophan (W) or a phenylalanine (F) residue yields a polypeptide with a modified activity and/or stability.

In one embodiment, a polypeptide includes a substitution of at least one, at least two, at least three, or at least four arginine residues capable of being ADP-ribosylated with a tryptophan or a phenylalanine residue. The arginine residue that is capable of being ADP-ribosylated can be substituted with either a tryptophan or a phenylalanine at this position. In one specific, non-limiting example one arginine capable of being ADP-ribosylated can be substituted with a tryptophan. In another specific, non-limiting example, one arginine capable of being ADP-ribosylated can be substituted with a phenylalanine. In other specific, non-limiting examples two arginines capable of being ADP-ribosylated can be substituted with two tryptophans or two phenylalanines, or one tryptophan and one phenylalanine. Specific, non-limiting examples of a polypeptide with at least one arginine residue capable of being ADP-ribosylated include a defensin or an ADP-ribosyltransferase.

Polypeptides with R:W or R:F substitutions disclosed herein include polypeptides with antimicrobial activity. Specific, non-limiting examples of antimicrobial activity include the secretion of cytokines, chemotaxis of T cells, and neutrophil recruitment. In one embodiment, the polypeptide with antimicrobial activity is a defensin, such as an alpha defensin.

In one specific embodiment, the alpha defensin is a vertebrate polypeptide, such as a mammalian polypeptide. In one example, the alpha defensin polypeptide is from a human. In other examples, the alpha defensin polypeptide is from a monkey, a rabbit, a rat, a cat, a dog, a pig, a sheep, or a mouse. The alpha defensin can be a human neutrophil peptide (HNP)-1. The alpha defensin polypeptide can also be HNP-2, HNP-3, HNP-4, HD-5, HD-6, or Def-X.

The alpha defensins include HNP-1, HNP-2, HNP-3, and HNP-4. HNP-1, HNP-2, and HNP-3 are products of the same 94 amino acid prepro-protein. The preproprotein has the sequence:
MRTLAILAAILLVALQAQAEPLQA-
RADEVAAAPEQIAADIPEVVVS LAWDESLAPKH
PGSRKNMDCYCRIPACIAGER-
RYGTCIYQGRLWAFCC; (SEQ ID NO:1, see also GenBank Accession No. P11479, herein incorporated by reference)
or a conservative variant thereof.

HNP-1 is one member of the family of alpha defensins produced by cleavage of the preproprotein. In one embodiment, HNP-1 has a sequence as set forth as:

ACYCRIPACIAGERRYGTCIYQGRLWAFCC;    (SEQ ID NO: 2)

or a conservative variant thereof.

At least one of the arginine residues at positions 5, 14, 15, or 24 (counting from the amino terminal end of the HNP-1 polypeptide sequence) of the HNP-1 polypeptide sequence as set forth as SEQ ID NO:2 is capable of being ADP-ribosylated. Thus, at least one of the arginine residues at position 5, 14, 15, or 24 can be substituted with a tryptophan or a phenylalanine residue to produce an antimicrobial polypeptide with increased stability and/or antimicrobial activity. Thus, in one embodiment a tryptophan is included in the HNP-1 polypeptide in at least one of positions 5, 14, 15, or 24. In another embodiment a phenylalanine is substituted for an arginine residue in at least one of positions 5, 14, 15, or 24. In a further embodiment the HNP-1 polypeptide includes the substitution of at least one tryptophan and at least one phenylalanine with an arginine that is capable of being ADP-rybosylated.

Specific, non-limiting examples of HNP-1 polypeptides with at least one R:F or R:W substitution are shown in the table below.

TABLE 1

| | SEQ ID NO: 2 Position No.: | | | |
|---|---|---|---|---|
| | 5 | 14 | 15 | 24 |
| Native (SEQ ID NO: 2) | R | R | R | R |
| Substitution | W | R | R | R |
| Substitution | R | W | R | R |
| Substitution | R | R | W | R |
| Substitution | R | R | R | W |
| Substitution | F | R | R | R |
| Substitution | R | F | R | R |
| Substitution | R | R | F | R |
| Substitution | R | R | R | F |
| Substitution | W | F | R | R |
| Substitution | F | W | R | R |
| Substitution | R | R | F | W |
| Substitution | R | R | W | F |
| Substitution | R | W | F | R |
| Substitution | R | F | W | R |
| Substitution | F | F | F | F |
| Substitution | W | W | W | W |
| Substitution | W | W | F | F |
| Substitution | F | F | W | W |
| Substitution | F | F | F | W |
| Substitution | F | W | F | F |
| Substitution | F | F | W | F |
| Substitution | W | F | F | F |
| Substitution | W | W | W | F |
| Substitution | W | W | F | W |
| Substitution | W | F | W | W |
| Substitution | F | W | W | W |
| Substitution | W | R | R | F |
| Substitution | R | W | F | R |
| Substitution | F | R | R | W |
| Substitution | W | R | R | F |

HNP-2 is another member of the family of alpha defensins produced by cleavage of the preproprotein. In one embodiment, HNP-2 has a sequence as set forth as:

CYCRIPACIAGERRYGTCIYQGRLWAFCC;    (SEQ ID NO: 3)

or a conservative variant thereof.

At least one of the arginine residues at positions 4, 13, 14, or 23 (counting from the amino terminal end of the HNP-2 polypeptide sequence) of the HNP-2 polypeptide sequence as in SEQ ID NO:3 is capable of being ADP-ribosylated. Thus, at least one of the arginine residues at positions 4, 13, 14, or 23 capable of being ADP-ribosylated can be substituted with either a tryptophan or a phenylalanine residue to produce an antimicrobial polypeptide with increased stability and/or antimicrobial activity. One of skill in the art can readily identify polypeptides encompassed by the description set forth herein to generate exemplary substitutions similar to those shown in Table 2, below.

TABLE 2

| | SEQ ID NO: 3 Position No.: | | | |
| --- | --- | --- | --- | --- |
| | 4 | 13 | 14 | 23 |
| Native (SEQ ID NO: 3) | R | R | R | R |
| Substitution | W | R | R | R |
| Substitution | R | W | R | R |
| Substitution | R | R | W | R |
| Substitution | R | R | R | W |
| Substitution | F | R | R | R |
| Substitution | R | F | R | R |
| Substitution | R | R | F | R |
| Substitution | R | R | R | F |
| Substitution | W | F | R | R |
| Substitution | F | W | R | R |
| Substitution | R | R | F | W |
| Substitution | R | R | W | F |
| Substitution | R | W | F | R |
| Substitution | R | F | W | R |
| Substitution | F | F | F | F |
| Substitution | W | W | W | W |
| Substitution | W | W | F | W |
| Substitution | F | F | W | W |
| Substitution | F | F | F | W |
| Substitution | F | W | F | F |
| Substitution | F | F | W | F |
| Substitution | W | F | F | F |
| Substitution | W | W | W | F |
| Substitution | W | W | F | W |
| Substitution | W | F | W | W |
| Substitution | F | W | W | W |
| Substitution | W | R | R | F |
| Substitution | R | W | F | R |
| Substitution | F | R | R | W |
| Substitution | W | R | R | F |

HNP-3 is a third member of the family of alpha defensins produced by cleavage of the preproprotein. In one embodiment, HNP-3 has a sequence as set forth as:

```
DCYCRIPACIAGERRYGTCIYQGRLWAFCC;    (SEQ ID NO: 4)
``` or a conservative variant thereof.

At least one of the arginine residues at positions 5, 14, 15, or 24 (counting from the amino terminal end of the HNP-3 polypeptide sequence) of the HNP-3 polypeptide sequence as in SEQ ID NO:4 is capable of being ADP-ribosylated. Thus, at least one of the arginine residues at positions 5, 14, 15, or 24 is capable of being ADP-ribosylated and can be substituted with either a tryptophan or a phenylalanine residue to produce an antimicrobial polypeptide with increased stability and/or increased antimicrobial activity. One of skill in the art can readily identify polypeptides encompassed by the description set forth herein to generate exemplary substitutions, such as those shown in Table 3, below.

TABLE 3

| | SEQ ID NO: 4 Position No.: | | | |
| --- | --- | --- | --- | --- |
| | 5 | 14 | 15 | 24 |
| Native (SEQ ID NO: 4) | R | R | R | R |
| Substitution | W | R | R | R |
| Substitution | R | W | R | R |
| Substitution | R | R | W | R |
| Substitution | R | R | R | W |
| Substitution | F | R | R | R |
| Substitution | R | F | R | R |
| Substitution | R | R | F | R |
| Substitution | R | R | R | F |
| Substitution | W | F | R | R |
| Substitution | F | W | R | R |
| Substitution | R | R | F | W |
| Substitution | R | R | W | F |
| Substitution | R | W | F | R |
| Substitution | R | F | W | R |
| Substitution | F | F | F | F |
| Substitution | W | W | W | W |
| Substitution | W | W | F | F |
| Substitution | F | F | W | W |
| Substitution | F | F | F | W |
| Substitution | F | W | F | F |
| Substitution | F | F | W | F |
| Substitution | W | F | F | F |
| Substitution | W | W | W | F |
| Substitution | W | W | F | W |
| Substitution | W | F | W | W |
| Substitution | F | W | W | W |
| Substitution | W | R | R | F |

HNP-4 is an alpha defensin that is the product of a preproprotein having a sequence as set forth as:

MRIIALLAAILLVALQVRAG-
PLQARGDEAGQEQRGPEDQDISISFAWDKS
SALQVSG STRGMVCSCRLVFCRRTELRVGN-
CLIGGVSFTYCCTRVD (SEQ ID NO:5, see also GenBank Accession No. NP_001916, herein incorporated by reference)

or a conservative variant thereof.

In one embodiment, HNP-4 has a sequence as set forth as:

```
VCSCRLVFCRRTELRVGNCLIGGVSFTYCCTRVD;    (SEQ ID NO: 6)
``` or a conservative variant thereof.

At least one of the arginine residues at positions 5, 10, 11, 15, or 32 (counting from the amino terminal end of the HNP-4 polypeptide sequence) of the HNP-4 polypeptide sequence is capable of being ADP-ribosylated. Thus, at least one of the arginine residues at positions 5, 10, 11, 15, or 32 is capable of being ADP-ribosylated and can be substituted with either a tryptophan or a phenylalanine residue to produce an antimicrobial polypeptide with increased stability and/or antimicrobial activity. One of skill in the art can readily identify polypeptides encompassed by the description set forth herein to generate exemplary substitutions similar to those shown in Tables 1, 2, or 3.

HD-5 is produced by cleavage of the following preproprotein having a sequence as set forth as:

MRTIAILAAILLVALQAQAES LQERADEATTQKQS-
GEDNQDLAISFAGNGLSALRTS GSQARATCY-
CRTGRCATRESLSGVCEISGRLYRLCCR; (SEQ ID NO:7, GenBank Accession No. NP_066290, herein incorporated by reference)

or conservative variants thereof.

In one embodiment, HD-5 has a sequence as set forth as:

```
TCYCRTG RCATRESLSG VCEISGRLYR LCCR;    (SEQ ID NO: 8)
``` or conservative variants thereof.

At least one of the arginine residues at positions 5, 8, 12, 24, 27, or 31 (counting from the amino terminal end of the HNP-5 polypeptide sequence) of the HNP-5 polypeptide sequence as in SEQ ID NO:8 is capable of being ADP-ribosylated. Thus, at least one of the arginine residues at positions 5, 8, 12, 24, 27, or 31 is capable of being ADP-ribosylated and can be substituted with a tryptophan or a phenylalanine residue to produce an antimicrobial polypeptide with increased stability or antimicrobial activity. One of skill in the art can readily identify polypeptides encompassed by the description set forth herein to generate exemplary substitutions similar to those shown in Tables 1, 2, or 3.

HD-6 is produced by cleavage of the following preproprotein having a sequence as set forth as:
MRTLTILTAVLLVALQAKAEPLQAED-
DPLQAKAYEADAQEQRGANDQDFAVSFAE
DASSSLRALGSTRAFTCHCRRSCYSTEY-
SYGTCTVMGINHRFCCL; (SEQ ID NO:9, GenBank Accession No. NP_001917, herein incorporated by reference)

In one embodiment, HD-6 has a sequence as set forth as:

```
TCHCRRSCYS TEYSYGTCTV MGINHRFCCL;    (SEQ ID NO: 10)
``` or a conservative variant thereof.

At least one of the arginine residues at positions 5, 6, or 26 (counting from the amino terminal end of the HNP-6 polypeptide sequence) of the HNP-6 polypeptide sequence as in SEQ ID NO:10 is capable of being ADP-ribosylated. Thus, at least one of the arginine residues at positions 5, 6, or 26 is capable of being ADP-ribosylated and can be substituted with a tryptophan or a phenylalanine residue to produce an antimicrobial polypeptide with increased stability and/or antimicrobial activity. One of skill in the art can readily identify polypeptides encompassed by the description set forth herein to generate exemplary substitutions similar to those shown in Tables 1, 2, or 3.

Any ADP-ribose acceptor that contains an arginine residue capable of being ADP-ribosylated can be substituted with a tryptophan or a phenylalanine residue to produce an antimicrobial polypeptide with increased stability and/or antimicrobial activity. In one embodiment, a polypeptide with an R:W or an R:F substitution, where the arginine residue is capable of being ADP-ribosylated, is a polypeptide with NADase activity. In another embodiment, a polypeptide with an R:W or an R:F substitution, where the arginine residue is capable of being ADP-ribosylated, is a polypeptide with ART activity, such as an ART. Two specific, non-limiting examples of a polypeptide with ART activity include ART2a and ART2b. Other specific, non-limiting examples of polypeptides with ART activity include, but may not be limited to, ART1, ART3, ART4, or ART5. In one embodiment, ART is a vertebrate polypeptide. In another embodiment, ART is a mammalian polypeptide. In yet another embodiment, ART is a rat polypeptide, for example ART2b.

The polypeptides disclosed herein can be produced by any method known to one of skill in the art. In one embodiment, the polypeptide is synthetic. Synthetic polypeptides having fewer than about 100 amino acids, or fewer than about 50 amino acids, and can be generated using known techniques. For example, solid phase techniques, such as the Merrifield solid-phase synthesis method (Merrifield, *J. Am. Chem. Soc.* 85:2149-2146, 1963), can be used to generate synthetic polypeptides. Equipment for automated synthesis is commercially available (e.g. Perkin Elmer, Applied BioSystems). These automated synthesizers can be used to produce substitutions (such as an R:W or R:F substitution) of the peptide sequence of interest.

Polypeptides including an R:W or an R:F substitution of an arginine was capable of being ADP-ribosylated can be produced recombinantly using a DNA sequence that encodes the polypeptide, which can be inserted into an appropriate expression vector. Methods are known to construct expression vectors encoding a polypeptide of interest and appropriate transcriptional and translational control elements. In addition, methods are known to one of skill in the art that are of use to produce site-directed mutations in a nucleic acid sequence of interest, such that translation of the sequence includes R:W or R:F substitution. Materials can also be synthesized chemically without requiring recombinant DNA. This is especially true, but not limited to, small peptides or other arginine-containing compounds as noted above.

Method of Producing a Polypeptide with Modified Activity and/or Stability

A method is provided herein to produce a polypeptide with modified activity and/or stability. The method includes substituting an arginine residue that is capable of being ADP-ribosylated, with a tryptophan or a phenylalanine residue in the amino acid sequence of the polypeptide. In one embodiment, the polypeptide is an antimicrobial polypeptide. Specific, non-limiting examples of an antimicrobial polypeptide are a defensin or an ADP-ribosyltransferase. The method to produce a polypeptide with modified stability or activity can include substituting at least one, at least two, at least three, or at least four arginine residues that are capable of being ADP-ribosylated with a tryptophan or a phenylalanine residue within the amino acid sequence of a polypeptide. Thus, in one example a polypeptide can be produced in which with one arginine capable of being ADP-ribosylated is substituted with a tryptophan. In another example a polypeptide can be produced in which one arginine capable of being ADP-ribosylated is substituted with a phenylalanine. In other examples two arginines capable of being ADP-ribosylated are substituted with two tryptophans or two phenylalanines. In a further example at least one arginine capable of being ADP-ribosylated is substituted with a phenylalanine and at least one arginine capable of being ADP-ribosylated is substituted with a tryptophan.

In one embodiment, the method produces a polypeptide with increased activity, compared to a control polypeptide, by making an R:W substitution or an R:F substitution of an arginine capable of being ADP-ribosylated. In another embodiment, the method produces a polypeptide with a decreased activity of the polypeptide, compared to a control polypeptide. In one example, the increased activity is an enzymatic activity such as, but not limited to, NADase activity. In other examples, the increased activity is ART activity, recruitment of an immune cell, cytokine secretion, or an antimicrobial or cytotoxic activity. The activity (for example the antimicrobial activity or the lysis of a pathogen in response to administration of the protein) can be increased by at least about 20%, at least about 50%, at least about 80%, or at least about 100%. In another embodiment, the activity can be decreased by at least about 20%, at least about 50%, at least about 80%, or at least about 100%.

A method is also provided for producing a polypeptide with increased stability. The method includes producing a polypeptide with an R:W or an R:F substitution of an arginine capable of being ADP-ribosylated. A specific, non-limiting example of a control polypeptide is the wildtype polypeptide including an arginine at the position of interest where the arginine is unsubstituted or ADP-ribosylated. Another example of a control is a standard value. In several embodiments, the increase in stability can be at least about a 20%, at least about a 50%, at least about an 80%, or at least about a 100% increase in stability.

A substitution of an amino acid residue within a polypeptide, such as the substitution of an arginine residue capable of being ADP-ribosylated, with a tryptophan or a phenylalanine residue, can be accomplished by any means known to one of skill in the art. As described above, either genetic engineering or chemical synthesis techniques can be used. In one specific, non-limiting example, standard DNA mutagenesis techniques include oliogonucleotide and PCR-mediated site-directed mutagenesis. Details of these techniques are provided in Sambrook et al. (In *Molecular Cloning: A Laboratory Manual*, CSHL, New York, 2001), Ch. 13. In addition, as described above, amino acid substitutions can be introduced by the chemical synthesis of molecules with the desired amino acids at the specified residue position.

Method of Screening

Disclosed herein are methods for screening a polypeptide to determine if the polypeptide can be stabilized or if the activity of the polypeptide can be altered. In one embodiment, the ability of an arginine residue to be ADP-ribosylated is an indication that the polypeptide can be stabilized or that the activity of the polypeptide can be increased. In one example, the polypeptide can be an antimicrobial polypeptide such as a defensin. The polypeptide can alternatively be an enzyme, such as an ADP-ribosyltransferase.

One skilled in the art can readily determine if an arginine is ADP-ribosylated. In one specific, non-limiting example, the polypeptide is incubated with an ART capable of ADP-ribosylating an arginine residue. The ability of ART to ADP-ribosylate the polypeptide is then assessed. The polypeptide can have at least one, such as at least two, at least three, or at least four, arginine residues that are capable of being ADP-ribosylated. Any assay can be used to assess ADP-ribosylation such as, but not limited to, measurements of the electrophoretic mobility of the polypeptide, compared to that of a control polypeptide. A decrease in the electrophoretic mobility of the polypeptide, compared to the control polypeptide, is an indication that the polypeptide is ADP-ribosylated. A specific, non-limiting example of a control polypeptide is a polypeptide known not to be ADP-ribosylated, such as a polypeptide that has been incubated with a buffer (in place of the ART). Another specific, non-limiting example of a control polypeptide is a polypeptide with an R:F and/or an R:W substitution, wherein the arginine is not capable of being ADP-ribosylated.

In order to confirm that the polypeptide identified in the screening method has altered stability or activity, the arginine residue is substituted with a tryptophan or a phenylalanine. At least one, at least two, at least three, or at least four arginine residues can be substituted with a tryptophan or a phenylalanine residue and it can be determined if this polypeptide has a change in stability or activity. In one embodiment, the stability of a polypeptide is increased by an amino acid substitution, such as an R:F or an R:W substitution, such as at least about a 20%, 50%, 80%, 100% or 200% increase, as compared to an unsubstituted polypeptide or to a control polypeptide. Stability can be measured by any means known to one of skill in the part, and includes, but is not limited to, measurements of half-life (t½) of the polypeptide. The activity of the polypeptide with the R:W or the R:F substitution can also be measured and compared to the stability of a control polypeptide. A specific, non-limiting example of a control is a polypeptide that has an arginine at one or more positions of interest, or a standard value.

A polypeptide with at least one, at least two, at least three, or at least four R:W or R:F substitutions, can be tested to determine if they have an altered activity. In one embodiment, the activity of a polypeptide is increased by an amino acid substitution, such as an R:F or an R:W substitution, such as at least about a 20%, 50%, 80%, 100% or 200% increase, as compared to ac control polypeptide, such as an unsubstituted polypeptide. In another embodiment, the activity of a polypeptide is decreased by an amino acid substitution, such as an R:F or an R:W substitution, such as at least about a 20%, 50%, 80%, or 100% decrease, as compared to a control polypeptide, such as an unsubstituted polypeptide, or a standard value.

Activity can be measured by any means known to one of skill in the art, and includes, but is not limited to, an enzymatic activity or an immunologic activity. Assays to measure enzymatic activity include kinase assays (such as serine/threonine or tyrosine kinase assays), autophosphorylation assays, phosphatase assays, NADase assay, ADP-ribosyltransferase assays, phosphodiesterase assays, glutamic acid decarboxylase assays, oxygenoase assays. Assays to measure immunologic activity include chemotaxis assays, cytokine production and secretion assays, biological assays for T-cell activity including assays for cytotoxic activity, Th1 activity and Th2 activity, assays for neutrophil recruitment, and assays to measure B-cell activation. Other enzymatic and immunologic assays are known to those of skill in the art.

Pharmaceutical Compositions and Methods of Using Substituted Polypeptides

As disclosed herein, the amino acid substitution of an arginine residue that is capable of being ADP-ribosylated can alter the activity of the polypeptide or can alter the stability of the polypeptide. For example, the arginine-to-tryptophan (R:W) substitution or an arginine-to-phenylalanine (R:F) substitution in an antimicrobial peptide, such as a defensin molecule, can increase the antimicrobial activity of the peptide and/or modify an immune response in a subject when a therapeutically effective amount is administered to a subject. Thus, a method is provided herein for modulating an immune response against a microbe.

Defensin polypeptides are antimicrobial peptides that are involved in innate immune defense and are cytotoxic for microbes such as bacteria, fungi, and certain types of viruses. In addition, they stimulate IL-8 release from neighboring cells and induce an increase in T cell chemotaxis. As disclosed in the methods described above, the activity of a defensin molecule can also be altered by substituting an arginine residue with a tryptophan or a phenylalanine residue, where the arginine residue is a residue that is capable of being ADP-ribosylated. Moreover, the R:W and/or R:F substituted defensin molecule can have an increased antimicrobial activity compared to the defensin molecule with an ADP-ribosylated arginine residue. The activity profile of the defensin molecule can also be altered. The R:W and/or R:F substituted defensin molecule can have an increased stability compared to a defensin molecule that includes an ADP-ribosylated arginine residue.

In one embodiment, substituting an arginine residue with a tryptophan or a phenylalanine residue, where the arginine residue is capable of being ADP-ribosylated, increases the anti-microbial activity of the defensin, compared to an unsubstituted defensin molecule when administered to a subject. In several specific, non-limiting examples the alpha defensin includes, but is not limited to, HNP-1, HNP-2, HNP-3, and HNP-4. The antimicrobial activity can be antibacterial, antifungal, or antiviral activity. In several specific, non-limiting examples, the increase in antimicrobial activity is at least about 20%, at least about 50%, at least about 80%, at least about 100%, or at least about 200%. In another embodiment, the increased antimicrobial activity is an increase in cytokine production. The increase in cytokine expression can be an increase in cytokine secretion, expression, and/or release. In one specific, non-limiting example, the cytokine is IL-8. The antimicrobial activity can be an increase in recruitment of inflammatory cells, such as neutrophils. Neutrophil recruitment can be measured by any method known to one of skill in the art. In one embodiment, promotion of neutrophil recruitment is measured by the release of IL-8 from cells. In one specific, non-limiting example, IL-8 release is measured by indirect enzyme-linked immunosorbent assay (ELISA).

In yet another embodiment, the altered antimicrobial activity is an increase in inflammatory cell chemotaxis. In one specific, non-limiting example the inflammatory cells are T cells.

Thus, a method of modifying an immune response against a microbe is provided. The method includes administering a therapeutically effective amount of a defensin with an R:W substitution and/or an R:F substitution, where the arginine residue is capable of being ADP-ribosylated, to a subject infected with or at risk of being infected with the microbe, thereby modulating the immune response against the microbe. The immune response in the subject is increased, as compared to a subject treated with an unsubstituted defensin molecule, or an untreated subject.

In one embodiment, modification of an immune response includes increasing lymphocyte chemotaxis. Thus, the administration of a therapeutically effective amount of a defensin to a subject, such as an alpha defensin with an R:W substitution or an R:F substitution where the arginine is capable of being ADP-ribosylated, modulates T cell chemotaxis in the subject. For example, T-cell chemotaxis is increased in a subject following substitutions of a modified alpha defensin, compared to an unsubstituted alpha defensin molecule. T cell chemotaxis can be measured by any means known to one of skill in the art, but is generally measured by measuring the length of migration of the T cells, the number of migrating T cells, or both. In one specific, non-limiting example, T cell migration is measured in vitro, such as by measuring T cell migration from one cell culture chamber to another cell culture chamber through a porous membrane.

In another embodiment, modification of the immune response includes altering an inflammatory response. Thus, the administration of a therapeutically effective amount of a defensin, such as an alpha defensin, results in an increase in an inflammatory response. An inflammatory response can be measured by any means known to one of skill in the art. In one embodiment, an inflammatory response is measured by assessing the number of activated T cells present in the sample. In another embodiment, an inflammatory response is measured by a change in neutrophil recruitment. In yet another embodiment, an inflammatory response is measured by cytokine production and/or release, such as a change in IL-8 production and/or release. In several embodiments, increased cytokine production and/or release is a 100%, 200%, or 300% increase in cytokine production and/or release in the presence of a defensin with an R:W substitution or an R:F substitution, where the arginine residue is capable of being ADP-ribosylated, compared to a control.

The subject can be any mammal. In one embodiment, the subject is a human. In other embodiments, the subject may be a monkey, a rabbit, a rat, a pig, a sheep, a dog, a cat, or a mouse. In one embodiment, the subject is suffering from a disease, such as a pulmonary disease. Specific, non-limiting examples of pulmonary diseases are emphysema, adult respiratory distress syndrome, asthma, bronchopulmonary dysplasia, chronic bronchitis, sarcoidosis, pulmonary fibrosis, or cystic fibrosis. In another embodiment, the subject is infected with a pathogen, such as a bacteria, fungus, or virus. Specific, non-limiting examples of bacterial infections affecting the lungs are pneumonia or tuberculosis.

In another embodiment, the subject has a tumor, such as a benign or a malignant tumor. Specific, non-limiting examples are lung, intestine, colon, breast, ovarian, uterine, prostate, testicular, or liver tumors.

In a further embodiment, the subject has an intestinal disease. Specific, non-limiting examples of intestinal diseases are inflammatory bowel diseases such as Crohn's Disease and ulcerative colitis.

In yet another embodiment, the subject is immunodeficient. In one specific, non-limiting example, the subject is infected with an immunodeficiency virus, such as a human immunodeficiency virus (e.g., HIV-1 or HIV-2). In a further embodiment, the subject has an autoimmune disorder.

Pharmaceutical compositions can include a therapeutically effective amount of a polypeptide with an R:W or an R:F substitution, where the arginine residue is capable of being ADP-ribosylated, and can be formulated with an appropriate solid or liquid carrier, depending upon the particular mode of administration chosen. Specific, non-limiting examples of polypeptides with an R:W or an R:F substitution that have an altered activity or stability include alpha defensin and ART. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

Other medicinal and pharmaceutical agents, for instance other immunostimulants, also can be included. Immunostimulants include, but are not limited to, Macrophage Inflammatory Protein (MIP)-β, IL-1, IL-8, IL-10, granulocyte-macrophage colony stimulating factor, granulocyte colony stimulating factor, neurokinin, and tumor necrosis factor-alpha, for example.

The dosage form of the pharmaceutical composition will be determined by the chosen mode of administration to the subject. For instance, in addition to injectable fluids, topical, inhalation, oral and suppository formulations can be employed. Topical preparations can include eye drops, ointments, sprays and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a therapeutically effective amount of a polypeptide, such as an alpha defensin, with an R:W or an R:F substitution, where the arginine residue is capable of being ADP-ribosylated, can be formulated in unit dosage form, suitable for individual administration of precise dosages. In one specific, non-limiting example, a unit dosage can contain from about 1 ng to about 1 mg of such a polypeptide. The amount of active compound(s) administered will be dependent on the subject being treated, the severity of the affliction, and the manner of administration, and, for example, can be determined at the judgment of the prescribing clinician. Within these bounds, the formulation to be administered will contain a quantity of the active component(s) in amounts effective to achieve the desired effect in the subject being treated.

The compounds of this disclosure can be administered to humans or other animals on whose tissues they are effective in various manners such as topically, orally, intravenously, intramuscularly, intraperitoneally, intranasally, intradermally, intrathecally, subcutaneously, via inhalation or via suppository. The particular mode of administration and the dosage regimen will be selected by the attending clinician, taking into account the particulars of the case (e.g. the subject, the disease, the disease state involved, and whether the treatment is prophylactic). Treatment can involve daily or multi-daily doses of compound(s) over a period of a few days to months, or even years during the course of treatment. However, the effective amount of the defensin is dependent on the subject being treated, the severity and type of the affliction, and the manner of administration of the therapeutic(s).

A therapeutically effective amount of a polypeptide, such as an alpha defensin, with an R:W or an R:F substitution, of an arginine residue capable of being ADP-ribosylated, can be the amount of a polypeptide necessary to modulate the immune system of a subject. In several examples, a therapeutically effective amount is an amount of the substituted defensin sufficient to stimulate antimicrobial activity, such as an amount sufficient to stimulate T cell chemotaxis or promote neutrophil recruitment.

Site-specific administration of the disclosed compounds can be used, for instance by applying the amino acid substituted defensin polypeptide (for example an R:W or an R:F substituted alpha defensin, of an arginine residue capable of being ADP-ribosylated) to a region of inflammation, a region of infection, or a region suspected of being prone to inflammation or infection.

The present disclosure also includes combinations of a polypeptide, such as an alpha defensin, with an R:W or an R:F substitution, of the arginine residue capable of being ADP-ribosylated, with one or more other agents useful in the treatment of an immune-related disorder, condition, or disease. For example, the compounds of this disclosure can be administered in combination with effective doses of immunostimulants, anti-cancer agents, anti-inflammatory agents, anti-infectives, and/or vaccines. The term "administration in combination" or "co-administration" refers to both concurrent and sequential administration of the active agents. A subject that is infected with an infectious agent, or displays an immune suppression, will be a candidate for treatment using the therapeutic methods of the disclosed herein, as described below.

Additional Methods

A method is disclosed herein for inhibiting the cytotoxic activity of a native alpha defensin polypeptide in a subject. The method includes administering to a subject a therapeutically effective amount of a defensin polypeptide with an arginine-to-tryptophan (R:W) or an arginine-to-phenylalanine (R:F) substitution, where the arginine residue is capable of being ADP-ribosylated, to decrease the cytotoxic activity of the polypeptide. In one embodiment, the defensin polypeptide with an R:W or an R:F substitution, where the arginine residue is capable of being ADP-ribosylated, is an alpha defensin polypeptide. For example, if the alpha defensin polypeptide is HNP-1, the arginine residue at position 14 of the HNP-1 sequence set forth as SEQ ID NO:1 (or a conservative variant thereof) is capable of being ADP-ribosylated and can be substituted with a tryptophan residue. In another example, an arginine residue at position 14 is substituted with a phenylalanine residue.

Cytotoxic activity is measured by the ability of an alpha defensin polypeptide to lyse a cell. In several embodiments, the lysed cell is a normal cell, a malignant cell, or a cell that is resistant to host defense mechanisms. Cell lysis can be measured by any means known to detect the number of viable cells remaining in a sample, following an incubation period. The number of viable cells in the sample is compared to a control sample. For example, the control can be the number of cells remaining following incubation with a wildtype alpha defensin.

A method is also provided herein for modulating an activity, such as the NADase activity or a tranferase activity, of an ART. In one embodiment, an R:W substitution and/or an R:F substitution, where the arginine residue is capable of being ADP-ribosylated, increases the NADase activity of the ART. In another embodiment, an R:W substitution and/or an R:F substitution, where the arginine residue is capable of being ADP-ribosylated, increases the transferase activity of the ART. In several specific examples, the ART is ART-1, ART-2a, ART-2b, ART-3, ART-4, and ART-5.

In several specific, non-limiting examples, the increase in NADase or ART activity is increased at least about 20%, at least about 50%, at least about 80%, at least about 100%, or at least about 200%, compared to a control polypeptide. NADase activity can be measured by any means known to one of skill in the art, such as measuring an increase in the amount of hydrolyzed $NAD^+$. ART activity can be measured by any means known to one of skill in the art, including detecting an increase in the amount ADP-ribosylated arginine residues.

The disclosure is illustrated by the following non-limiting Examples.

EXAMPLES

Although ADP-ribosylation of specific residues is known to alter the properties of modified proteins, the ADP-ribose bond is readily cleaved by pyrophosphatases. Thus, there exists a need to identify additional, stable, protein modifications that have an effect on protein activity.

Mono-ADP-ribosyltransferases catalyze the transfer of ADP-ribose from NAD to one of several specific amino acids in an acceptor protein. In place of an amino acid, some of these enzymes utilize water as an acceptor, generating ADP-ribose and nicotinamide from NAD (NADase activity). The properties of these enzymes have been most studied in the bacterial toxins (e.g., cholera toxin (CT), an arginine-specific ADP-ribosyltransferase (ART)) that uses ADP-ribosylation to modify proteins that alter activity of critical metabolic or regulatory pathways in mammalian cells (*ADP-ribosylating toxins and G proteins: Insights in Signal Transduction* (Moss, J., and Vaughan, M., eds.), American Society for Microbiology, Washington, D.C., 1990).

One family of mammalian ARTs have precursor forms with signal sequences responsible for export into the ER lumen at the amino termini and in some cases, signal sequences necessary for addition of a glycosylphosphatidylinositol (GPI) anchor, at the carboxy termini (Okazaki et al., *J Biol Chem* 273(37):23617-20, 1998). Because of their extracellular localization, these ARTs can potentially regulate cell-cell and cell-matrix interactions through modification of ecto- or extracellular proteins. For example, ART1 modifies integrin α7 in C2C12 cells (Zolkiewska et al., *J Biol Chem* 268(34):25273-6, 1993), and co-receptors of the TCR (e.g., LFA-1, CD8, CD27, CD45) in mouse T lymphocytes (Nemoto et al., *J Immunol* 157(8):3341-9, 1996). These modifications, which have been identified in cell culture, require extracellular NAD at millimolar concentrations. Extracellular proteins, such as defensins that participate in the innate immune response, are ADP-ribosylated by ecto-transferases with resulting alteration in their biological properties. An ADP-ribosylated HNP-1 was recovered from human bronchoalveolar lavage fluid consistent with its in vivo modification. An ecto-ART that catalyzes this modification has been identified on human airway epithelial cells, suggesting that the airway might utilize an ADP-ribosylation pathway to regulate the immune response (Balducci et al., *Am J Respir Cell Mol Biol* 21(3):337-46, 1999).

The amino acid sequences of the ARTs differ significantly from those of the toxins and each other. ART1 from rabbit skeletal muscle is 30-40% identical in sequence to rat ART2 NADase (RT6) (Balducci et al., *Am J Respir Cell Mol Biol* 21(3):337-46, 1999). Analysis of the crystallographic structure of toxin ADP-ribosyltransferases identified three regions involved in formation of the catalytic site, NAD binding, and activation of the ribosyl-nicotinamide bond, which is required for ADP-ribose transfer (Domenighini et al., *Mol Microbiol* 21(4):667-74, 1996 and Bredehorst et al., *Adv Exp Med Biol* 419:185-9, 1997). These regions appear to be present in the mammalian transferases as well (Moss et al., *Mol Cell Biochem* 193(1-2):109-13, 1999). Region I is defined by an arginine (R) or histidine (H), Region II, by a sequence rich in hydrophobic amino acids, or by serine (S) X S, (where X represents threonine (T), serine (S) or alanine (A)), and Region III by glutamate (E). In ART1 and the bacterial toxins, site-specific mutagenesis of Region III verified the importance of Region III glutamate in catalysis and defined a role for a second glutamate in Region III (Takada et al., *J Biol Chem* 269(13):9420-3, 1994). Replacement of the second glutamate of human ART1 in the consensus E-X-E sequence abolished activity. In mouse ART2a (mRt6.1) replacement of the first glutamate with glutamine (Q) abolished the arginine-specific transferase activity giving rise to an NADase (Karsten et al., *Adv Exp Med Biol* 419:175-80, 1997), suggesting that the carboxyl group of the first glutamate was necessary for proper positioning of the guanidino group of arginine. The converse was true as well: the rat ART2 NADase was converted to an arginine-specific transferase by replacing the first glutamine with glutamate (Hara et al., *J Biol Chem* 271(47):29552-5, 1996).

Rat ART2b (RT6.2) and ART2a (RT6.1) are encoded by two alleles of a single copy gene (Thiele et al., *Adv Exp Med Biol* 419:109-20, 1997); the human counterpart has stop signals in the coding region and no protein is expressed (Haag et al., *J Mol Biol* 243(3):537-46, 1994). To date, only post-thymic peripheral and intestinal intraepithelial T lymphocytes are known to express ART2 proteins (Mojcik et al., *Dev Immunol* 1(3):191-201, 1991). Both ART2 proteins appear to be released from cells in vivo and have been found in soluble form in the high-density lipoprotein fraction of serum (Lesma et al., *J Immunol* 161(3):1212-9, 1998 and Waite et al., *Cell Immunol* 152(1):82-95, 1993). Although their biological functions are unknown, the absence, depletion or reduction of ART2-expressing T lymphocytes is associated with autoimmune diabetes (Bortell et al., *Autoimmunity* 33(3):199-211, 2001 and Greiner et al., *J Immunol* 136(1):148-51, 1986). Both proteins are linked to the cell surface by GPI-anchors, and ART2a, but not ART2b, is glycosylated (Thiele et al., *Immunology* 59(2):195-201, 1986 and Koch et al., *Immunology* 65(2):259-65, 1988). In their mature processed forms, ART2b and ART2a differ by ten amino acids. Because of the glutamine in Region III (QEE), ART2 catalyzes the hydrolysis of NAD to ADP-ribose and nicotinamide but, in contrast to ART1, does not transfer ADP-ribose to arginine or other small guanidino compounds. The proteins differed significantly in their abilities to catalyze auto-modification, with ART2b, but not ART2a, capable of auto-ADP-ribosylation at multiple sites. Auto-ADP-ribosylation has been reported to regulate NADase and transferase activities, most notably those of an erythrocyte NADase, the activity of which is decreased by auto-ADP-ribosylation (Yamada et al., *Arch Biochem Biophys* 308(1):31-6, 1994; Han et al., *Biochem J* 318(Pt 3):903-8, 1996; and Weng et al., *J Biol Chem* 274(45): 31797-803, 1999).

As described in the Examples set forth below, to investigate the structural requirements for auto-ADP-ribosylation and its effects on activity, the amino acid sequences of ART2b and ART2a were compared, paying particular attention to the critical catalytic Region III. Replacement of arginine 204 with lysine (R204K) abolished both the primary and secondary modifications. Replacement with tryptophan, however, (R204W) resulted in auto-ADP-ribosylation at non-arginine sites, suggesting that the hydrophobic tryptophan could substitute for an ADP-ribosyl-arginine, consistent with a regulatory role for amino acid 204 in modification of sites elsewhere in the protein.

Example 1

Materials and Methods

Construction of Wild Type ART2a (RT6.1) and ART2b (RT6.2) Expression Plasmids

Rat ART2a open reading frame was amplified by PCR using an ART2a-pCRII.1plasmid as a template and cloned in the pMAMneo mammalian expression vector (Clontech, Palo Alto, Calif.) as an NheI/XhoI fragment carrying a Kozak consensus region (GCCACG) upstream of the first codon. Construction of the rat ART2b-pMAMneo mammalian expression vector was previously described (Takada et al., *J. Biol. Chem.* 269:9420-9423, 1994). To improve the level of expression of recombinant ART2b in mammalian cells, a Kozak consensus sequence was placed upstream of the first ATG, using the QuickChange site-directed mutagenesis kit (Stratagene, La Jolla, Calif.), according to the manufacturer's instructions with a pair of complementary mutant primers corresponding to the following sequence:
CGGACTCACCATAGGGACCAAGCTAGC-
CGCCATGCC ATCAAATATTTGCAAGTTCTTCC (SEQ ID NO:13). Plasmid construct sequences were verified by DNA sequencing of the entire open reading frame.

The amino acid sequences of rat ART2b and ART2a differ considerably from those of bacterial toxins and other mammalian ADP-ribosyltransferases, although each has large regions of similarity to rabbit ART 1 and the bacterial toxins, particularly, in three regions believed to be involved in formation of the NAD-binding site. The sequences of ART2b and ART2a differ by fourteen amino acids, ten of which are located N-terminal to the region excised during addition of the GPI-anchor (FIG. 1). In ART2b, but not other ARTs, an arginine is present at position 204 (R204) at the amino end of Region III, which contains the consensus glutamate (position 209 in ART2) required for catalytic activity; a putative consensus glycosylation site is present at positions 58-60 in ART2a but not in ART2b.

Site-directed Mutagenesis of Wild Type RT6.1 and RT6.2

Both ART2b and ART2a have NADase activity, but only ART2b is significantly auto-ADP-ribosylated. To investigate the structural basis for these differences in catalytic function, site-specific mutagenesis was employed with synthesis of recombinant ART2b and ART2a proteins in rat adenocarcinoma (NMU) cells under a dexamethasone-sensitive promoter. Point mutations were introduced in ART2a and ART2b cDNAs using the QuickChange site-directed mutagenesis kit (Stratagene, La Jolla, Calif.) according to the manufacturer's instructions. Sequences of sense strands from which pairs of complementary mutation primers were synthesized to produce the indicated changes in amino acids are indicated in Tables 4 and 5, below. Altered bases are underlined.

TABLE 4

Mutation primers for ART2a

| Amino acid substitution | Sequence | SEQ ID NO: |
|---|---|---|
| N58A | CCCTGCTTTTAAAGGAAGACTTTGCTAAGAGTGA GAAATTAAAAGTTGCG | 14 |
| K59M, S60N, E61A | CCCTGCTTTTAAAGGAAGACTTTAATATGAATGC GAAATTAAAAGTTGCG | 15 |
| M81R | CGATGGAACAACATAAAACCTAGTAGGAGTTATC CCAAAGGTTTCATTGATTTCC | 16 |
| Y204R | GGGGGTTTATATCAAAGAATTCTCTTTCCGTCCT GACCAAGAGGAGGTG | 17 |

TABLE 5

Mutation primers for ART2b

| Amino acid substitution | Sequence | SEQ ID NO: |
|---|---|---|
| R81K | CGATGGAACAACATAAAACTAGTAAGAGTTATCC CAAAGGTTTCAATGATTTC | 18 |
| R204K | GGGGGTTTATATCAAAGAATTCTCTTTCAAGCCT GACCAAGAGGAGGTG | 19 |
| R204E | GGGGGTTTATATCAAAGAATTCTCTTTCGAGCCT GACCAAGAGGAGGTG | 20 |
| R204Y | GGGGGTTTATATCAAAGAATTCTCTTTCTACCCT GACCAAGAGGAGGTG | 21 |
| R204W | GGGGGTTTATATCAAAGAATTCTCTTTCTGGCCT GACCAAGAGGAGGTG | 22 |

All clones were screened by restriction digestion and confirmed by DNA sequencing (both strands) of the entire open reading frames.

Cell Culture and Protein Expression

Rat mammary adenocarcinoma (NMU) cells were grown in Eagle's minimal essential medium with 10% fetal calf serum (GIBCO BRL, Carlsbad, Calif.) at 37° C. in 5% $CO_2$. Cells were transfected with the pMAMneo vector (Clontech, Palo Alto, Calif.) containing the ART2a or ART2b construct as indicated using the Lipofectomine Plus Reagent (Invitrogen, Carlsbad, Calif.) according to manufacturer's instructions. Transfected cells were selected with Geneticin (G-418; Life Technologies, Inc, Grand Island, N.Y.), 0.5 mg/ml.

Protein expression was induced with 1 µM dexamethasone (Sigma, St. Louis, Mo.) for 24 hours. Trypsinized confluent cells were sedimented by centrifugation (1000×g), washed with DPBS, and incubated (1 hour, 37° C.) with 0.05 units of phosphatidylinositol-specific phospholipase C(PI-PLC) (ICN Pharmaceuticals, Costa Mesa, Calif.) in 500 µl of DPBS to cleave the GPI anchor and release the protein from the cell surface. Cells were sedimented by centrifugation (1000×g), and the supernatant containing transferase protein linked to the C-terminal oligosaccharide was collected.

NAD Glycohydrolase and ADP-ribosyltransferase Assays

NADase activity was measured in DPBS with 0.1 mM [carbonyl-$^{14}$C]NAD ($8 \times 10^4$ cpm) for 1 hour at 30° C., (total volume=150,u). Samples (50,u) were applied to AG1-X2 (BIO-RAD, Hercules, Calif.) columns (0.4×4 cm), equilibrated and eluted with water for liquid scintillation counting as described (Moss et al., *Proc Natl Acad Sci U S A* 73(12): 4424-7, 1976). Transferase activity was assayed similarly with or without 20 mM agmatine as ADP-ribose acceptor and with [adenine-$^{14}$C]NAD substituted for [carbonyl-$^{14}$C]NAD.

Example 2

Sequence Comparison of ART2b and ART2a

The amino acid sequences of rat ART2b and ART2a differ considerably from those of bacterial toxins and other mammalian ADP-ribosyltransferases, although each has large regions of similarity to rabbit ART 1 and the bacterial toxins, particularly, in three regions believed to be involved in formation of the NAD-binding site. The sequences of ART2b and ART2a differ by fourteen amino acids, ten of which are located N-terminal to the region excised during addition of the GPI-anchor (FIG. 1). In ART2b but not other ARTs, an arginine is present at position 204 (R204) at the amino end of Region III, which contains the consensus glutamate (position 209 in ART2) required for catalytic activity; a putative consensus glycosylation site is present at positions 58-60 in ART2a but not in ART2b.

Example 3

Site Specific Mutagenesis

Amino Acid Substitutions

Both ART2b and ART2a have NADase activity, but only ART2b is significantly auto-ADP-ribosylated. To investigate the structural basis for these differences in catalytic function, site-specific mutagenesis was employed with synthesis of recombinant ART2b and ART2a proteins in rat adenocarcinoma cells (NMU) under a dexamethasone-sensitive promoter. After induction and expression of the GPI-anchored proteins, cells were incubated with PI-PLC to cleave the GPI anchor and then [$^{32}$P]-NAD was added to the medium to promote auto-ADP-ribosylation of the released protein (FIG. 2). All recombinant proteins had NADase activity and all were reactive with antipeptide antisera NAD2, exhibiting the expected size of 29 kDa on immunoblots. ART2a, the glycosylated isoform, had an additional band at approximately 33 kDa, consistent with its single consensus sequence for N-glycosylation.

Figure 3:
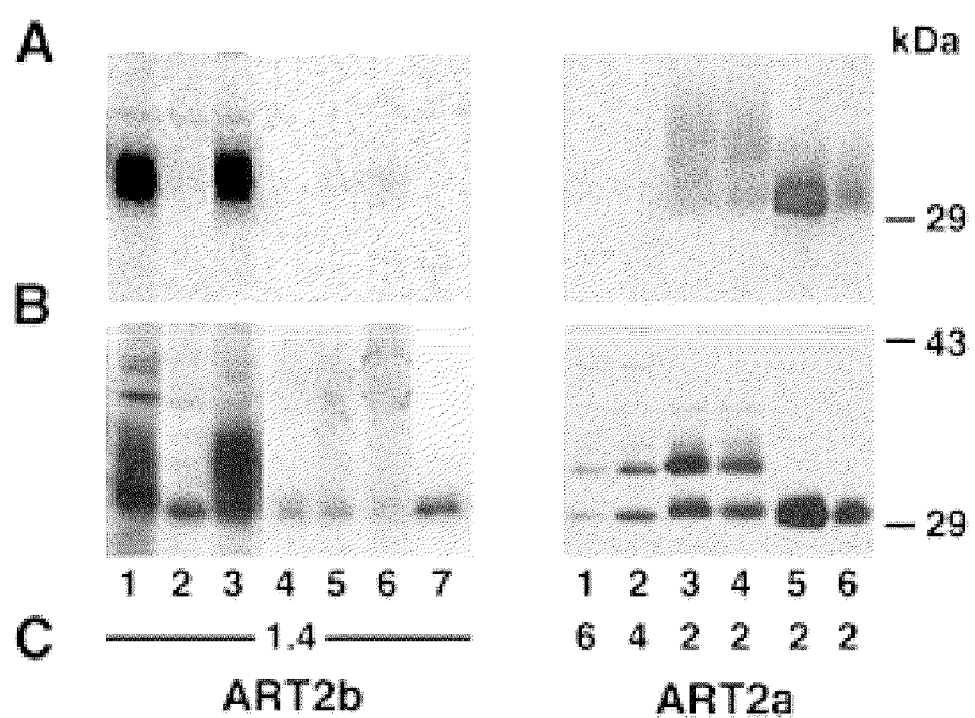
FIG. 3 is a digital image of a set of blots demonstrating the auto-ADP-ribosyltransferase activity (FIG. 3A) and immunoreactivity (FIG. 3B), as well as data demonstrating the NAD glycohydrolase (NADase) activity (nmol per hour) (FIG. 3C) of ART2b, ART2a, and various mutant forms of these proteins. The left column shows data for the following wild-type and mutant ART2b proteins: ART2b (lane 1), ART2b(R204K) (lane 2), ART2b(R81K) (lane 3), ART2b (R204Y) (lane 4), ART2b(R204E) (lane 5), ART2b(R204W) (lane 6), ART2b(R81K,R204K) (lane 7). The right column shows data for the following wild-type and mutant ART2a proteins: ART2a (lane 1), ART2a(M81R) (lane 2), ART2a (Y204R) (lane 3), ART2a(M81R,Y204R) (lane 4), ART2a (N58A,Y204R) (lane 5), ART2a(59NMA61,Y204R) (lane 6). Data shown are representative of two experiments.

Multiple species of auto-ADP-ribosylated wild-type ART2b were observed by SDS-PAGE. Substitution of lysine for arginine 81 had no effect on auto-ADP-ribosylation whereas it was abolished by replacement of arginine-204 by lysine (R204K) (FIG. 2), consistent with arginine-204 being the primary modification site. As expected (and shown in FIG. 5), the ADP-ribosylarginine bond was sensitive to hydroxylamine. Replacement of R204 with Y, E and K in ART2b(R81K) (FIG. 3) abolished auto-ADP-ribosylation, although all proteins retained NADase activity. Wild-type ART2a with tyrosine in position 204 was not significantly auto-modified. However, in ART2a(Y204R) or ART2a (M81R,Y204R), auto-ADP-ribosylation of both glycosylated 33 kDa and nonglycosylated 29 kDa forms was observed (FIG. 3). The substitution of arginine at position 81 alone, ART2a(M81R), had no effect.

NADase activities of all ART2a mutants were lower than that of wild-type ART2a, independent of their ability to be auto-ADP-ribosylated. These results were consistent with a role for position 204 in regulating NADase activity. In ART2a (Y204R), modification of the putative consensus glycosylation site, replacing N58 with A, or changing 59KSE61 to 59MNA61, prevented glycosylation, resulting in a single immunoreactive band after SDS-PAGE. Both non-glycosylated species were auto-ADP-ribosylated. Thus, a single amino acid, R204, is responsible for auto-ADP-ribosylation of ART2b or ART2a(Y204R).

Example 4

Auto-ADP-Ribosylation

Figure 4:
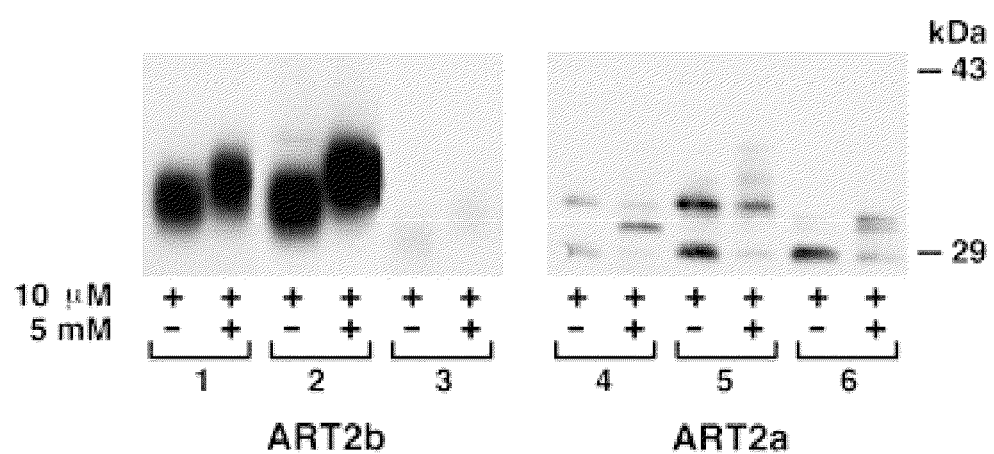
FIG. 4 is a digital image of a set of blots demonstrating the auto-ADP-ribosylation of ART2b (FIG. 4A), ART2a (FIG. 4B), and their various mutant forms. The gels contain samples from cells expressing ART2b wild-type (lane 1), ART2b (R81K) (lane 2), ART2b(R204W) (lane 3), ART2a(Y204R) (lane 4), ART2a(Y204R,M81R) (lane 5) and ART2a (59NMA61,Y204R) (lane 6). Data represent one of two experiments.
Figure 5:
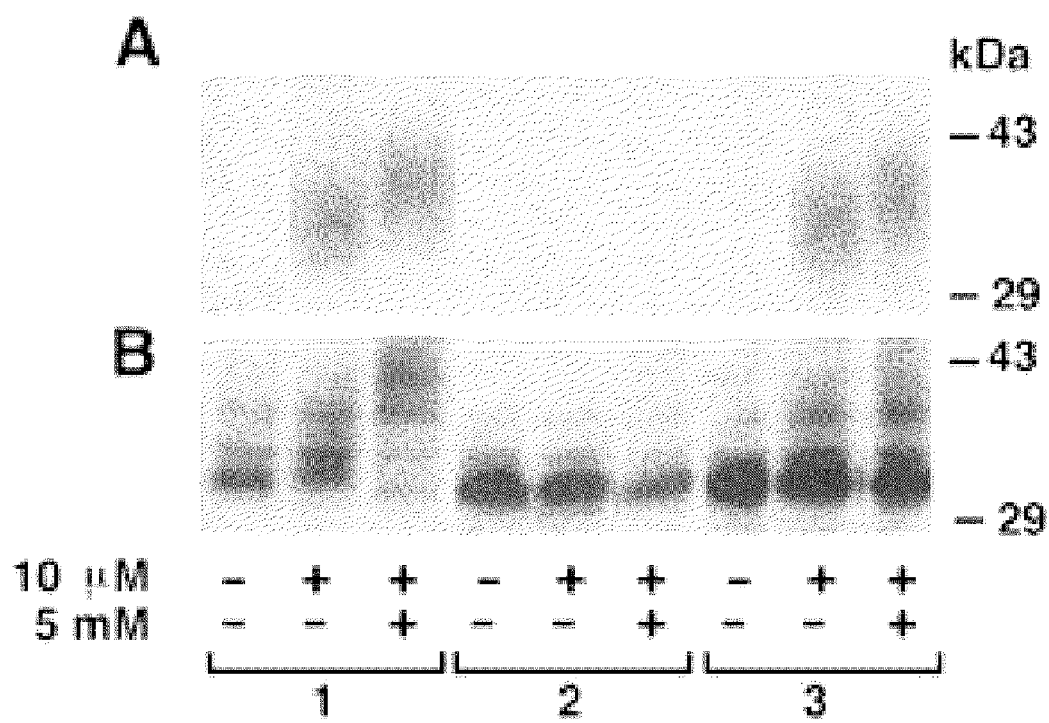
FIG. 5 is a digital image of a set of blots demonstrating the SDS-PAGE separation of auto-ADP-ribosylated ART2b and ART2b(R204K) proteins as analyzed by a phosphorimager (FIG. 5A) and by immunoreactivity (FIG. 5B). The blots contain samples from cells expressing wild type ART2b (lanes 1), ART2b(R204K) (lanes 2), or a mixtures of samples containing ART2b and ART2b(R204K) (lanes 3). Samples were incubated with or without 10 μM [$^{32}$P]NAD followed by either TCA precipitation or further incubation with 5 mM NAD. The radiolabeled wild type ART2b and ART2b (R204K) proteins were combined and then incubated with or without 5 mM NAD.

To assess the ability of ART2 proteins, ART2a and ART2b, to be auto-ADP-ribosylated at multiple sites, proteins were incubated first with 10 µM [$^{32}$P]NAD, followed by addition of 5 mM unlabeled NAD and further incubation (FIG. 4). Wild-type ART2b, ART2b(R81K) and mutants ART2a(Y204R), ART2a(Y204R,M81R) and ART2a(59MNA61,Y204R), exhibited auto-ADP-ribosylation following incubation with 5 mM NAD as evidenced by a decrease in mobility on SDS-PAGE, consistent with modification of multiple sites. In contrast, ART2b(R204K) was not modified by incubation with NAD, suggesting that primary and secondary auto-ADP-ribosylation sites were lost (FIG. 5). It is unlikely that auto-modification was due to non-enzymatic addition of [$^{32}$P] ADP-ribose since reactions were carried out in the presence of 1 mM ADP-ribose, or due to NAD binding, since the radiolabel was not displaced by incubation with 5 mM NAD.

Thus, arginine at position 204 regulates the auto-ADP-ribosylation of multiple sites in ART2b and ART2a(Y204R). Since lysine, a conservative substitution, could not replace arginine, ADP-ribosylation of arginine appears to be an initiating event required for modifications elsewhere in the protein. When multiple auto-ADP-ribosylation sites were seen on SDS-PAGE, a decrease in the rate of NAD hydrolysis by wildtype ART2b was observed. The activity of wildtype ART2b decreased during the course of the reaction, as did ART2b(R204W), while that of ART2b(R204K), which is not auto-ADP-ribosylated, did not change.

These data suggest that the residues which are auto-modified have access to the catalytic site, and hence, can be modified, can regulate auto-ADP-ribosylation activity as in the case of ART2a(Y204R), and can modulate NADase activity. Without being bound by theory, one possible reason for this in ART2a is because of the proximity of the residues to Region III glutamate. All ART2a mutants capable of auto-ADP-ribosylation (i.e., arginine at position 204) had reduced NADase activity compared to wild-type (FIG. 3).

Example 5

Ribosylation of ART2b(R204K) and Characterization of ADP-Ribose Bonds

To investigate whether ART2b(R204K) could be modified, wildtype ART2b was incubated with its mutant ART2b (R204K) and millimolar NAD (FIG. 5). Following incubation with NAD with or without ART2b(R204K), ART2b exhibited decreasing mobility on SDS-PAGE, indicating that it was auto-ADP-ribosylated. The migration of ART2b(R204K), however, was unchanged, consistent with the conclusion that ART2b(R204K) is not modified by wildtype ART2b in an intermolecular reaction.

Figure 6:
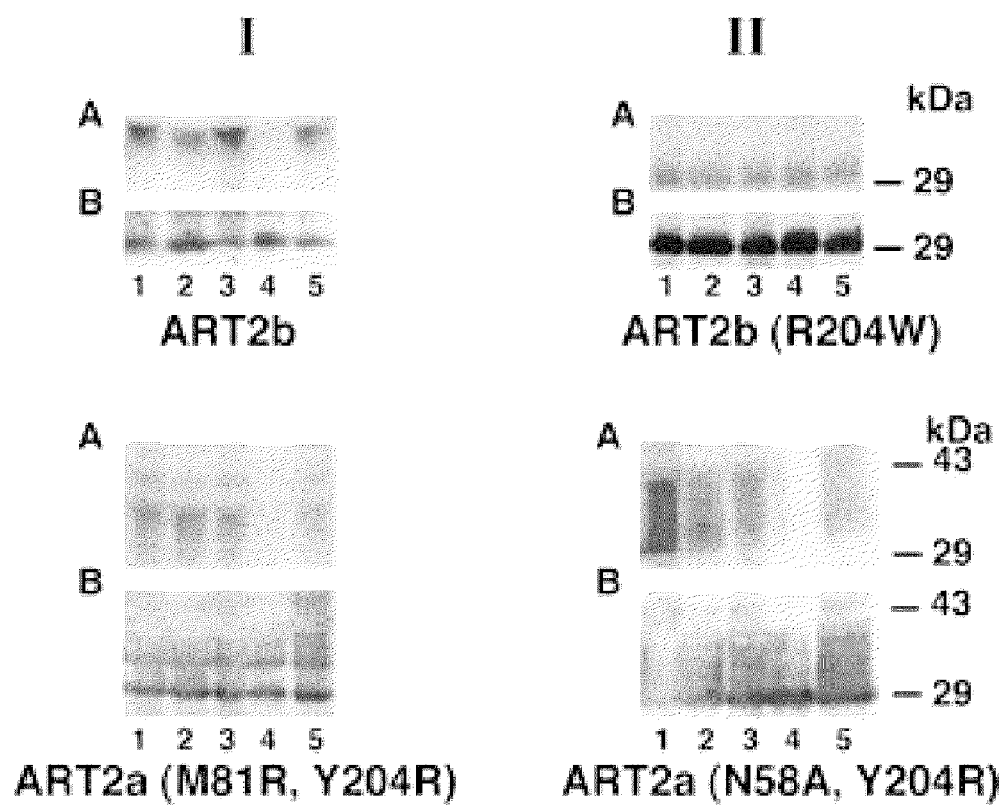
FIG. 6 is a digital image of a set of blots demonstrating the SDS-PAGE separation of proteins tested for their sensitivity to acid, hydroxylamine and mercuric chloride. Samples from cells expressing wild-type ART2b, ART2b(R204W), ART2a (M81R,Y204R) and ART2a(N58A,Y204R) were auto-ADP-ribosylated with 10 μM[$^{32}$P]NAD followed by addition of 10% TCA (column II), or further incubation with 5 mM NAD at 30° C. for 1 hour before precipitation with 10% TCA (column I). Neutralized samples were suspended in 0.1M Tris-HCl pH 7.5 (lane 1), 0.2M HCl (lane 2), 10 mM HgCl$_2$ (lane 3), 2M NH$_2$OH (lane 4), or 0.2M NaCl (lane 5) for 2 hours at 37° C. The samples were separated by SDS-PAGE in 12% gels, transferred to nitrocellulose and analyzed by phosphorImager (FIG. 6A) and by immunoblot with antipeptide antibody 1126 (FIG. 6B). Data are from one experiment, representative of two.

An ADP-ribose-amino acid linkage can be characterized by its sensitivity to acid, hydroxylamine, and mercuric chloride (FIG. 6). To characterize the multiple ADP-ribose bonds that result from incubation of wildtype ART2b, or ART2a (M81R,Y204R) with millimolar NAD, their chemical sensitivity was tested. The PI-PLC released proteins were incubated with 10 µM [$^{32}$P]NAD, [RT6.1(N58A, Y204R) and RT6.2(R204W)], or also followed by 5 mM NAD. For auto-ADP-ribosylated ART2b, ART2a(M81R,Y204R) and RT6.1 (N58A,Y204R), hydroxylamine released the [$^{32}$P]ADP-ribose radiolabel, consistent with the chemical stability of an ADP-ribose-arginine linkage.

Surprisingly, as disclosed herein, a mutant ART2b with tryptophan replacing arginine-204, ART2b(R204W), had weak auto-ADP-ribosylation activity at multiple sites with NADase activity greater than that of wild-type ART2b (FIGS. 3,4). [$^{32}$P]ADP-ribose was not released from auto-ADP-ribosylated ART2b(R204W) by hydroxylamine, mercury chloride or acid suggesting that arginine, cysteine, and lysine respectively were not modified by the auto-ADP-ribosylation reaction (FIG. 6). Thus, the tryptophan mutant is an auto-ADP-ribosyltransferase although it differs from wild-type ART2b in the ADP-ribose acceptor site(s). Without being bound by theory, the tryptophan may function in the regulatory role of an ADP-ribosylated arginine-204. The bulky side chain or hydrophobicity of tryptophan coupled with its position in Region III in proximity to the catalytic glutamate (amino acid 209) could promote auto-ADP-ribosyltransferase, as well as NADase activity. The mutant, like the wild-type, however, is unable to transfer ADP-ribose to agmatine.

The ability of tryptophan to replace some of the function of ADP-ribosylarginine is likely to be of use in protein design. Although ADP-ribosylation has effects on protein function, the modification itself is unstable in biological systems. It can be cleaved by pyrophosphatases, with release of AMP, and the resulting phospho-ribosyl protein, further degraded by phosphatases, yielding ribosyl-protein. Obviously, synthesis of ADP-ribosylated proteins requires an additional step(s) following production of a recombinant molecule. In contrast, a protein containing tryptophan can be produced by standard techniques and should have no unusual instability in biological systems. As disclosed herein, replacement of an arginine that is capable of being ribosylated with a tryptophan or a phenylalanine finds use in many systems, including, but not limited to, the defensins, as described below.

Example 6

Cytotoxicity Assay

The antibacterial activity of different concentrations (16, 32, 64, 128, 256 nM) of HNP-1, ADP-ribosyl-HNP-1, or HNP-1 with either a R:W substitution or a R:F substitution, on *Escherichia coli* ATCC43827 (American Type Culture Collection, Rockville, Md.) is evaluated by the radial diffusion assay (Takemura et al., "Evaluation of susceptibility of gram positive and negative bacteria to human defensins by using radial diffusion assay," *Antimicrob. Agents Chemother.* 40:2280-2284, 1996). The results indicate that HNP-1 with an R:W substitution or an R:F substitution behaves in a manner similar to ADP-ribosylated HNP-1, which is less cytotoxic than unmodified HNP-1 for *E. coli* ATCC43827 in the radial diffusion assay (see PCT Application No. PCT/US03/04649, which is incorporated herein by reference).

Example 7

Chromium Release Assay

Chromium-labeled A549 cells (American Type Culture Collection) were incubated (18 hours, 37° C.) in 100 µl of serum-free RPMI (Gibco Fluids Inc., Rockville, Md.) containing HNP-1, ADP-ribosyl-HNP-1, or HNP-1 with either an R:W substitution or an R:F substitution (1.5 to 24 µM) to quantify defensin cytotoxicity. Cytotoxicity is measured as the amount of chromium released from the cells (Panyutich et al., "Human neutrophil defensins and serpins form complexes and inactivate each other," *Am. J. Respir. Cell. Mol. Biol.* 12:351-357, 1995). The results indicate that HNP-1 with either an R:W substitution or an R:F substitution and ADP-ribosylated HNP-1 are less cytotoxic than unmodified HNP-1 for A549 cells.

Example 8

Radial Diffusion and Chromium Release Assays

HNP-1 (100 nM) is incubated for 1 hour at 37° C. with ADP-ribosylated HNP-1, or HNP-1 with either an R:W substitution or an R:F substitution (0-800 nM) before the initiation of the cytotoxicity assay on *E. coli*.

HNP-1 (12 µM) is incubated with ADP-ribosyl-HNP-1, or HNP-1 with either an R:W substitution or an R:F substitution (1.5-12 µM) for 1 hour at 37° C. before the initiation of the chromium release assay.

ADP-ribosylated HNP-1 blocks the cytotoxic activity of HNP-1 in a concentration-dependent manner. HNP-1 with either an R:W substitution or an R:F substitution has the same effect on HNP-1 as ADP-ribosylated HNP-1.

Example 9

IL-8 Production by A549 Cells

A549 cells ($3 \times 10^4$ cells per well) are incubated in a 96-well plate in 200 µl of serum-free RPMI medium (Gibco Fluids Inc) containing ADP-ribosyl-HNP-1, HNP-1, or HNP-1 with either an R:W substitution or an R:F substitution (0.25, 0.75, 1.5, 3 mM). Culture medium is sampled after 12 or 24 hours of incubation and IL-8 content is assayed by indirect ELISA according to the manufacturer's instructions (R & D System Inc. Minneapolis, Minn.). At concentrations of 0.75 and 1.5 µM, IL-8 release is significantly higher with ADP-ribosylated HNP-1, or with HNP-1 with either an R:W substitution or an R:F substitution, than with the unmodified peptide.

Example 10

Chemotaxis Assay $CD3^+$ T-cells are isolated from human peripheral blood prepared by leukapheresis (NIH, Department of Transfusion Medicine, Bethesda, Md.) (Chertov et al., *J. Biol. Chem.* 271:2935-2940, 1996) and suspended in migration medium (RPMI 1640, 0.5% bovine serum albumin, 25 mM HEPES). Inserts coated with collagen IV (Becton Dickinson Labware, Bedford, Mass.) are placed into 24-well culture plates to form upper and lower chambers in each well. Upper chambers are wetted with migration medium, then 500 µl of migration medium with or without ADP-ribosyl-HNP-1, HNP-1, or with HNP-1 with either an R:W substitution or an R:F substitution (0.025 to 25 nM) are added to the lower chamber. Cells are added to the upper chamber and plates are incubated at 37° C. in 5% $CO_2$ for 4 hours. Lymphocytes that migrate to the lower chamber are harvested by centrifugation and counted in a hematocytometer. The results indicate that ADP-ribosyl HNP-1 and HNP-1 with either an R:W substitution or an R:F substitution retain their ability to recruit T cells.

This disclosure provides methods of producing polypeptides with arginine residues that are replaced with tryptophan or phenylalanine residues resulting in polypeptide with increased activity and/or stability. The disclosure further provides methods of screening for polypeptides that can be stabilized, as well as methods for modifying the activity of a polypeptide. It will be apparent that the precise details of the methods described may be varied or modified without departing from the spirit of the described invention. We claim all such modifications and variations that fall within the scope and spirit of the claims below.

We claim:

1. A substituted human defensin polypeptide, comprising:
   (i) a tryptophan residue or a phenylalanine residue substituted for at least one arginine residue in a corresponding non-substituted human alpha-defensin or human beta-defensin polypeptide;
   (ii) six conserved cysteine residues that form three disulfide bonds;
   (iii) decreased cytotoxic activity, compared to the corresponding non-substituted human defensin polypeptide; and
   (iv) increased polypeptide stability, compared to the corresponding non-substituted human defensin polypeptide, wherein the at least one arginine residue in the corresponding non-substituted human defensin polypeptide is ADP-ribosylated,
   wherein the polypeptide is no more than 94 amino acids in length and retains anti-microbial activity.

2. The substituted human defensin polypeptide of claim 1, wherein the polypeptide is no more than 50 amino acids in length.

3. The substituted human defensin polypeptide of claim 1, wherein a tryptophan residue is substituted for the at least one arginine residue.

4. The substituted human defensin polypeptide of claim 1, wherein a phenylalanine residue is substituted for the at least one arginine residue.

5. The substituted human defensin polypeptide of claim 2, wherein the polypeptide is between 29 and 34 or between 34 and 37 amino acids in length.

6. The substituted human defensin polypeptide of claim 1, wherein the corresponding non-substituted human defensin is an alpha defensin.

7. The substituted human defensin polypeptide of claim 6, wherein the alpha defensin is human neutrophil peptide (HNP)-1, HNP-2, HNP-3, HNP-4, human defensin (HD)-5, HD-6, or defensin-X.

8. A pharmaceutical composition comprising a therapeutically effective amount of the substituted human defensin polypeptide of claim 1.

9. The substituted human defensin polypeptide of claim 1, wherein the antimicrobial activity comprises chemotaxis of T cells, neutrophil recruitment or cytokine release.

10. The pharmaceutical composition of claim 8, wherein the antimicrobial activity comprises chemotaxis of T cells, neutrophil recruitment or cytokine release.

11. The substituted human defensin polypeptide of claim 7, wherein the substituted human defensin polypeptide comprises an amino acid sequence set forth as SEQ ID NO: 3 and wherein at least one arginine residue at position 4, 13, 14, or 23 of SEQ ID NO: 3 is substituted with a tryptophan residue or a phenylalanine residue.

12. The substituted human defensin polypeptide of claim 7, wherein the substituted human defensin polypeptide comprises an amino acid sequence set forth as SEQ ID NO: 6 and wherein at least one arginine residue at position 5, 10, 11, 15, or 32 of SEQ ID NO: 6 is substituted with a tryptophan residue or a phenylalanine residue.

13. The substituted human defensin polypeptide of claim 7, wherein the substituted human defensin polypeptide comprises an amino acid sequence set forth as SEQ ID NO: 8 and wherein at least one arginine residue at position 5, 8, 12, 24, 27, or 31 of SEQ ID NO: 8 is substituted with a tryptophan residue or a phenylalanine residue.

14. The substituted human defensin polypeptide of claim 7, wherein the substituted human defensin polypeptide comprises an amino acid sequence set forth as SEQ ID NO: 10 and wherein at least one arginine residue at position 5, 6, or 26 of SEQ ID NO: 10 is substituted with a tryptophan residue or a phenylalanine residue.

15. The pharmaceutical composition of claim 8, wherein the substituted human defensin polypeptide comprises an amino acid sequence set forth as SEQ ID NO: 3 and wherein at least one arginine residue at position 4, 13, 14, or 23 of SEQ ID NO: 3 is substituted with a tryptophan residue or a phenylalanine residue.

16. The pharmaceutical composition of claim 8, wherein the substituted human defensin polypeptide comprises an amino acid sequence set forth as SEQ ID NO: 6 and wherein at least one arginine residue at position 5, 10, 11, 15, or 32 of SEQ ID NO: 6 is substituted with a tryptophan residue or a phenylalanine residue.

17. The pharmaceutical composition of claim 8, wherein the substituted human defensin polypeptide comprises an amino acid sequence set forth as SEQ ID NO: 8 and wherein at least one arginine residue at position 5, 8, 12, 24, 27, or 31 of SEQ ID NO 8 is substituted with a tryptophan residue or a phenylalanine residue.

18. The pharmaceutical composition of claim 8, wherein the substituted human defensin polypeptide comprises an amino acid sequence set forth as SEQ ID NO: 10 and wherein at least one arginine residue at position 5, 6, or 26 of SEQ ID NO: 10 is substituted with a tryptophan residue or a phenylalanine residue.

19. The substituted human defensin polypeptide of claim 1, wherein the corresponding non-substituted human defensin is a beta defensin.

20. The substituted human defensin polypeptide of claim 19, wherein the beta defensin is human beta defensin1 (hBD1), hBD2, hBD3, or hBD4.

21. The substituted human defensin polypeptide of claim 11, wherein the substituted human defensin polypeptide comprises an amino acid sequence set forth as SEQ ID NO: 2 and wherein at least one arginine residue at position 5, 14, 15, or 24 of SEQ ID NO: 2 is substituted with a tryptophan residue or a phenylalanine residue.

22. The substituted human defensin polypeptide of claim 11, wherein the substituted human defensin polypeptide comprises an amino acid sequence set forth as SEQ ID NO: 4 and wherein at least one arginine residue at position 5, 14, 15, or 24 of SEQ ID NO: 4 is substituted with a tryptophan residue or a phenylalanine residue.

23. The substituted human defensin polypeptide of claim 11, wherein the substituted human defensin polypeptide comprises an amino acid sequence set forth as SEQ ID NO: 3 and wherein the arginine residue at position 13 of SEQ ID NO: 3 is substituted with a phenylalanine residue.

\* \* \* \* \*

UNITED STATES PATENT AND TRADEMARK OFFICE
CERTIFICATE OF CORRECTION

PATENT NO. : 7,923,535 B2  Page 1 of 2
APPLICATION NO. : 12/430023
DATED : April 12, 2011
INVENTOR(S) : Moss et al.

It is certified that error appears in the above-identified patent and that said Letters Patent is hereby corrected as shown below:

Column 15, lines 61-64, "MRTLAILAAILLVALQAQAEPLQA-RADEVAAAPEQIAADIPEVVVS LAWDESLAPKH PGSRKNMDCYCRIPACIAGER-RYGTCIYQGRLWAFCC;"

should read --MRTLAILAAILLVALQAQAEPLQARADEVAAAPEQIAADIP EVVVSLAWDESLAPKHPGSRKNMDCYCRIPACIAGERRYGTCIYQGRLWAFCC;--.

Column 18, lines 32-35, "MRIIALLAAILLVALQVRAG-PLQARGDEAGQEQRGPEDQDISISFAWDKS SALQVSG STRGMVCSCRLVFCRRTELRVGN-CLIGGVSFTYCCTRVD"

should read --MRIIALLAAILLVALQVRAGPLQARGDEAGQEQRGPEDQDISISF AWDKSSALQVSGSTRGMVCSCRLVFCRRTELRVGNCLIGGVSFTYCCTRVD--.

Column 18, lines 61-65, "MRTIAILAAILLVALQAQAES LQERADEATTQKQS-GEDNQDLAISFAGNGLSALRTS   GSQARATCY-CRTGRCATRESLSGVCEISGRLYRLCCR;"

should read --MRTIAILAAILLVALQAQAESLQERADEATTQKQSGEDNQDLAISF AGNGLSALRTSGSQARATCYCRTGRCATRESLSGVCEISGRLYRLCCR;--.

Column 28, lines 66-67 "CGGACTCACCATAGGGACCAAGCTAGC CGCCATGCC ATCAAATATTTGCAAGTTCTTCC"

should read --CGGACTCACCATAGGGACCAAGCTAGCCGCCATGCCATCAAA TATTTGCAAGTTCTTCC--.

Signed and Sealed this
Third Day of April, 2012

David J. Kappos
*Director of the United States Patent and Trademark Office*

CERTIFICATE OF CORRECTION (continued)
U.S. Pat. No. 7,923,535 B2

Column 30, line 27, "volume =150,u). Samples (50,u)" should read --volume =150 μl). Samples (50 μl)--.

SEQUENCE LISTING

<160> NUMBER OF SEQ ID NOS: 22

<210> SEQ ID NO 1
<211> LENGTH: 94
<212> TYPE: PRT
<213> ORGANISM: Homo sapiens

<400> SEQUENCE: 1

```
Met Arg Thr Leu Ala Ile Leu Ala Ala Ile Leu Val Ala Leu Gln
1               5                   10                  15

Ala Gln Ala Glu Pro Leu Gln Ala Arg Ala Asp Glu Val Ala Ala
                20                  25                  30

Pro Glu Gln Ile Ala Ala Asp Ile Pro Glu Val Val Val Ser Leu Ala
                35                  40                  45

Trp Asp Glu Ser Leu Ala Pro Lys His Pro Gly Ser Arg Lys Asn Met
    50                  55                  60

Asp Cys Tyr Cys Arg Ile Pro Ala Cys Ile Ala Gly Glu Arg Arg Tyr
65                  70                  75                  80

Gly Thr Cys Ile Tyr Gln Gly Arg Leu Trp Ala Phe Cys Cys
                85                  90

<210> SEQ ID NO 2
<211> LENGTH: 30
<212> TYPE: PRT
<213> ORGANISM: Homo sapiens

<400> SEQUENCE: 2

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 3
<211> LENGTH: 29
<212> TYPE: PRT
<213> ORGANISM: Homo sapiens

<400> SEQUENCE: 3

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
                20                  25

<210> SEQ ID NO 4
<211> LENGTH: 30
<212> TYPE: PRT
<213> ORGANISM: Homo sapiens

<400> SEQUENCE: 4

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 5
<211> LENGTH: 96
<212> TYPE: PRT
<213> ORGANISM: Homo sapiens

<400> SEQUENCE: 5

Met Arg Ile Ile Ala Leu Leu Ala Ala Ile Leu Leu Val Ala Leu Gln
1               5                   10                  15

Val Arg Ala Gly Pro Leu Gln Ala Arg Gly Asp Glu Ala Gly Gln Glu
                20                  25                  30

Gln Arg Gly Pro Glu Asp Gln Asp Ile Ser Ile Ser Phe Ala Trp Asp
                35                  40                  45

Lys Ser Ser Ala Leu Gln Val Ser Gly Ser Thr Arg Gly Met Val Cys
    50                  55                  60
```

Ser Cys Arg Leu Val Phe Cys Arg Arg Thr Glu Leu Arg Val Gly Asn
65                  70                  75                  80

Cys Leu Ile Gly Gly Val Ser Phe Thr Tyr Cys Cys Thr Arg Val Asp
            85                  90                  95

<210> SEQ ID NO 6
<211> LENGTH: 34
<212> TYPE: PRT
<213> ORGANISM: Homo sapiens

<400> SEQUENCE: 6

Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val Asp

<210> SEQ ID NO 7
<211> LENGTH: 94
<212> TYPE: PRT
<213> ORGANISM: Homo sapiens

<400> SEQUENCE: 7

Met Arg Thr Ile Ala Ile Leu Ala Ala Ile Leu Leu Val Ala Leu Gln
1               5                   10                  15

Ala Gln Ala Glu Ser Leu Gln Glu Arg Ala Asp Glu Ala Thr Thr Gln
            20                  25                  30

Lys Gln Ser Gly Glu Asp Asn Gln Asp Leu Ala Ile Ser Phe Ala Gly
        35                  40                  45

Asn Gly Leu Ser Ala Leu Arg Thr Ser Gly Ser Gln Ala Arg Ala Thr
    50                  55                  60

Cys Tyr Cys Arg Thr Gly Arg Cys Ala Thr Arg Glu Ser Leu Ser Gly
65                  70                  75                  80

Val Cys Glu Ile Ser Gly Arg Leu Tyr Arg Leu Cys Cys Arg
            85                  90

<210> SEQ ID NO 8
<211> LENGTH: 31
<212> TYPE: PRT
<213> ORGANISM: Homo sapiens

<400> SEQUENCE: 8

Thr Cys Tyr Cys Arg Thr Gly Arg Cys Ala Thr Arg Glu Ser Leu Ser
1               5                   10                  15

Gly Val Cys Glu Ile Ser Gly Arg Leu Tyr Arg Leu Cys Cys Arg
            20                  25                  30

<210> SEQ ID NO 9
<211> LENGTH: 100
<212> TYPE: PRT
<213> ORGANISM: Homo sapiens

<400> SEQUENCE: 9

Met Arg Thr Leu Thr Ile Leu Thr Ala Val Leu Leu Val Ala Leu Gln
1               5                   10                  15

Ala Lys Ala Glu Pro Leu Gln Ala Glu Asp Asp Pro Leu Gln Ala Lys
            20                  25                  30

Ala Tyr Glu Ala Asp Ala Gln Glu Gln Arg Gly Ala Asn Asp Gln Asp
        35                  40                  45

Phe Ala Val Ser Phe Ala Glu Asp Ala Ser Ser Ser Leu Arg Ala Leu

```
              50                  55                  60
Gly Ser Thr Arg Ala Phe Thr Cys His Cys Arg Arg Ser Cys Tyr Ser
 65                  70                  75                  80

Thr Glu Tyr Ser Tyr Gly Thr Cys Thr Val Met Gly Ile Asn His Arg
                 85                  90                  95

Phe Cys Cys Leu
            100

<210> SEQ ID NO 10
<211> LENGTH: 30
<212> TYPE: PRT
<213> ORGANISM: Homo sapiens

<400> SEQUENCE: 10

Thr Cys His Cys Arg Arg Ser Cys Tyr Ser Thr Glu Tyr Ser Tyr Gly
 1               5                  10                  15

Thr Cys Thr Val Met Gly Ile Asn His Arg Phe Cys Cys Leu
             20                  25                  30

<210> SEQ ID NO 11
<211> LENGTH: 275
<212> TYPE: PRT
<213> ORGANISM: Rattus norvegicus

<400> SEQUENCE: 11

Met Pro Ser Asn Ile Cys Lys Phe Phe Leu Thr Trp Trp Leu Ile Gln
 1               5                  10                  15

Gln Val Thr Gly Leu Thr Gly Pro Leu Met Leu Asp Thr Ala Pro Asn
             20                  25                  30

Ala Phe Asp Asp Gln Tyr Glu Gly Cys Val Asn Lys Met Glu Glu Lys
         35                  40                  45

Ala Pro Leu Leu Leu Lys Glu Asp Phe Asn Lys Ser Glu Lys Leu Lys
     50                  55                  60

Val Ala Trp Glu Glu Ala Lys Lys Arg Trp Asn Asn Ile Lys Pro Ser
 65                  70                  75                  80

Met Ser Tyr Pro Lys Gly Phe Asn Asp Phe His Gly Thr Ala Leu Val
                 85                  90                  95

Ala Tyr Thr Gly Ser Ile Gly Val Asp Phe Asn Arg Ala Val Arg Glu
            100                 105                 110

Phe Lys Glu Asn Pro Gly Gln Phe His Tyr Lys Ala Phe His Tyr Tyr
        115                 120                 125

Leu Thr Arg Ala Leu Gln Leu Leu Ser Asn Gly Asp Cys His Ser Val
    130                 135                 140

Tyr Arg Gly Thr Lys Thr Arg Phe His Tyr Thr Gly Ala Gly Ser Val
145                 150                 155                 160

Arg Phe Gly Gln Phe Thr Ser Ser Leu Ser Lys Thr Val Ala Gln
                165                 170                 175

Ser Pro Glu Phe Phe Ser Asp Asp Gly Thr Leu Phe Ile Ile Lys Thr
            180                 185                 190

Cys Leu Gly Val Tyr Ile Lys Glu Phe Ser Phe Tyr Pro Asp Gln Glu
        195                 200                 205

Glu Val Leu Ile Pro Gly Tyr Glu Val Tyr Gln Lys Val Arg Thr Gln
    210                 215                 220

Gly Tyr Asn Glu Ile Phe Leu Asp Ser Pro Lys Arg Lys Lys Ser Asn
225                 230                 235                 240

Tyr Asn Cys Leu Tyr Ser Ser Ala Gly Thr Arg Glu Ser Cys Val Ser
                245                 250                 255
```

```
Leu Phe Leu Val Val Leu Thr Ser Leu Leu Val Gln Leu Leu Cys Leu
            260                 265                 270

Ala Glu Pro
        275

<210> SEQ ID NO 12
<211> LENGTH: 275
<212> TYPE: PRT
<213> ORGANISM: Rattus norvegicus

<400> SEQUENCE: 12

Met Pro Ser Asn Ile Cys Lys Phe Phe Leu Thr Trp Trp Leu Ile Gln
  1               5                  10                  15

Gln Val Thr Gly Leu Thr Gly Pro Leu Met Leu Asp Thr Ala Pro Asn
             20                  25                  30

Ala Phe Asp Asp Gln Tyr Glu Gly Cys Val Asn Lys Met Glu Glu Lys
         35                  40                  45

Ala Pro Leu Leu Leu Gln Glu Asp Phe Asn Met Asn Ala Lys Leu Lys
     50                  55                  60

Val Ala Trp Glu Glu Ala Lys Lys Arg Trp Asn Asn Ile Lys Pro Ser
 65                  70                  75                  80

Arg Ser Tyr Pro Lys Gly Phe Asn Asp Phe His Gly Thr Ala Leu Val
                 85                  90                  95

Ala Tyr Thr Gly Ser Ile Ala Val Asp Phe Asn Arg Ala Val Arg Glu
            100                 105                 110

Phe Lys Glu Asn Pro Gly Gln Phe His Tyr Lys Ala Phe His Tyr Tyr
        115                 120                 125

Leu Thr Arg Ala Leu Gln Leu Leu Ser Asn Gly Asp Cys His Ser Val
    130                 135                 140

Tyr Arg Gly Thr Lys Thr Arg Phe His Tyr Thr Gly Ala Gly Ser Val
145                 150                 155                 160

Arg Phe Gly Gln Phe Thr Ser Ser Ser Leu Ser Lys Lys Val Ala Gln
                165                 170                 175

Ser Gln Glu Phe Phe Ser Asp His Gly Thr Leu Phe Ile Ile Lys Thr
            180                 185                 190

Cys Leu Gly Val Tyr Ile Lys Glu Phe Ser Phe Arg Pro Asp Gln Glu
        195                 200                 205

Glu Val Leu Ile Pro Gly Tyr Glu Val Tyr Gln Lys Val Arg Thr Gln
    210                 215                 220

Gly Tyr Asn Glu Ile Phe Leu Asp Ser Pro Lys Arg Lys Lys Ser Asn
225                 230                 235                 240

Tyr Asn Cys Leu Tyr Ser Ser Ala Gly Ala Arg Glu Ser Cys Val Ser
                245                 250                 255

Leu Phe Leu Val Val Leu Pro Ser Leu Leu Val Gln Leu Leu Cys Leu
            260                 265                 270

Ala Glu Pro
        275

<210> SEQ ID NO 13
<211> LENGTH: 59
<212> TYPE: DNA
<213> ORGANISM: Artificial sequence
<220> FEATURE:
<223> OTHER INFORMATION: Primer

<400> SEQUENCE: 13
cggactcacc ataggaccaa agctagccgc catgccatca aatatttgca agttcttcc        59
```

```
<210> SEQ ID NO 14
<211> LENGTH: 50
<212> TYPE: DNA
<213> ORGANISM: Artificial sequence
<220> FEATURE:
<223> OTHER INFORMATION: Primer

<400> SEQUENCE: 14
ccctgctttt aaaggaagac tttgctaaga gtgagaaatt aaaagttgcg            50

<210> SEQ ID NO 15
<211> LENGTH: 50
<212> TYPE: DNA
<213> ORGANISM: Artificial sequence
<220> FEATURE:
<223> OTHER INFORMATION: Primer

<400> SEQUENCE: 15
ccctgctttt aaaggaagac tttaatatga atgcgaaatt aaaagttgcg            50

<210> SEQ ID NO 16
<211> LENGTH: 55
<212> TYPE: DNA
<213> ORGANISM: Artificial sequence
<220> FEATURE:
<223> OTHER INFORMATION: Primer

<400> SEQUENCE: 16
cgatggaaca acataaaacc tagtaggagt tatcccaaag gtttcattga tttcc       55

<210> SEQ ID NO 17
<211> LENGTH: 49
<212> TYPE: DNA
<213> ORGANISM: Artificial sequence
<220> FEATURE:
<223> OTHER INFORMATION: Primer

<400> SEQUENCE: 17
gggggtttat atcaaagaat tctctttccg tcctgaccaa gaggaggtg             49

<210> SEQ ID NO 18
<211> LENGTH: 53
<212> TYPE: DNA
<213> ORGANISM: Artificial sequence
<220> FEATURE:
<223> OTHER INFORMATION: Primer

<400> SEQUENCE: 18
cgatggaaca acataaaact agtaagagtt atcccaaagg tttcaatgat ttc        53

<210> SEQ ID NO 19
<211> LENGTH: 49
<212> TYPE: DNA
<213> ORGANISM: Artificial sequence
<220> FEATURE:
<223> OTHER INFORMATION: Primer

<400> SEQUENCE: 19
gggggtttat atcaaagaat tctctttcaa gcctgaccaa gaggaggtg             49

<210> SEQ ID NO 20
<211> LENGTH: 49
<212> TYPE: DNA
<213> ORGANISM: Artificial sequence
<220> FEATURE:
<223> OTHER INFORMATION: Primer
```

```
<400> SEQUENCE: 20
gggggtttat atcaaagaat tctctttcga gcctgaccaa gaggaggtg                49

<210> SEQ ID NO 21
<211> LENGTH: 49
<212> TYPE: DNA
<213> ORGANISM: Artificial sequence
<220> FEATURE:
<223> OTHER INFORMATION: Primer

<400> SEQUENCE: 21
gggggtttat atcaaagaat tctctttcta ccctgaccaa gaggaggtg                49

<210> SEQ ID NO 22
<211> LENGTH: 49
<212> TYPE: DNA
<213> ORGANISM: Artificial sequence
<220> FEATURE:
<223> OTHER INFORMATION: Primer

<400> SEQUENCE: 22
gggggtttat atcaaagaat tctctttctg gcctgaccaa gaggaggtg                49
```